(12) United States Patent
Takahashi

(10) Patent No.: US 12,426,856 B2
(45) Date of Patent: Sep. 30, 2025

(54) THREE-DIMENSIONAL ULTRASOUND IMAGE GENERATION APPARATUS, THREE-DIMENSIONAL ULTRASOUND IMAGE GENERATION METHOD, AND THREE-DIMENSIONAL ULTRASOUND IMAGE GENERATION PROGRAM

(71) Applicant: FUJIFILM Corporation, Tokyo (JP)

(72) Inventor: Azuma Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 449 days.

(21) Appl. No.: 17/531,772

(22) Filed: Nov. 21, 2021

(65) Prior Publication Data

US 2022/0079561 A1 Mar. 17, 2022

Related U.S. Application Data

(63) Continuation of application No. PCT/JP2020/016817, filed on Apr. 17, 2020.

(30) Foreign Application Priority Data

Jun. 6, 2019 (JP) .................................. 2019-106449

(51) Int. Cl.
A61B 8/00 (2006.01)

(52) U.S. Cl.
CPC .............. *A61B 8/466* (2013.01); *A61B 8/483* (2013.01); *A61B 8/5246* (2013.01)

(58) Field of Classification Search
CPC ........ A61B 8/466; A61B 8/483; A61B 8/5246
See application file for complete search history.

(56) References Cited

U.S. PATENT DOCUMENTS

| 6,547,731 | B1 * | 4/2003 | Coleman | A61B 8/10 |
| | | | | 600/455 |
| 11,103,214 | B2 * | 8/2021 | Mine | A61B 8/4461 |

(Continued)

FOREIGN PATENT DOCUMENTS

| JP | 2003088521 | 3/2003 |
| JP | 2007236681 | 9/2007 |

(Continued)

OTHER PUBLICATIONS

Office Action of Japan Counterpart Application, with English translation thereof, issued on Nov. 15, 2022, pp. 1-8.

(Continued)

*Primary Examiner* — Adil Partap S Virk
(74) *Attorney, Agent, or Firm* — JCIPRNET

(57) ABSTRACT

A three-dimensional ultrasound image generation apparatus includes: an image acquisition unit that acquires a plurality of two-dimensional ultrasound images from each of a first viewpoint and a second viewpoint; a probe position information acquisition unit that acquires, for each imaging, position information of an ultrasound probe; a three-dimensional ultrasound image generation unit that generates three-dimensional ultrasound images; an organ extraction unit that extracts an organ included in the three-dimensional ultrasound images; an image processing unit that extracts an unclear image region from the three-dimensional ultrasound image from which at least the organ is extracted based on position information of the organ and the position information of the ultrasound probe and that performs suppression processing of suppressing unclearness; and an image combination unit that generates a combined three-dimensional ultrasound image by combining the three-dimensional ultrasound images from two viewpoints including the three- (Continued)

dimensional ultrasound image on which the suppression processing is performed.

7 Claims, 13 Drawing Sheets

(56) References Cited

U.S. PATENT DOCUMENTS

| | | | | |
|---|---|---|---|---|
| 2004/0254460 | A1* | 12/2004 | Burcher | A61B 5/6843 600/437 |
| 2007/0167801 | A1* | 7/2007 | Webler | G06T 19/00 600/459 |
| 2008/0283771 | A1* | 11/2008 | Li | A61B 8/4245 600/439 |
| 2009/0024030 | A1* | 1/2009 | Lachaine | A61B 8/14 600/437 |
| 2011/0125022 | A1* | 5/2011 | Lazebnik | A61B 8/4461 600/444 |
| 2011/0190629 | A1* | 8/2011 | Guenther | A61B 8/4245 600/437 |
| 2012/0157850 | A1* | 6/2012 | Sumi | A61B 8/145 600/443 |
| 2012/0265071 | A1* | 10/2012 | Berke | A61B 34/32 600/439 |
| 2012/0316407 | A1* | 12/2012 | Anthony | A61B 8/429 600/301 |
| 2014/0066770 | A1 | 3/2014 | Watanabe et al. | |
| 2014/0184600 | A1* | 7/2014 | Steen | G06T 15/08 345/424 |
| 2015/0031995 | A1* | 1/2015 | Guracar | G01S 7/52095 600/431 |
| 2015/0051489 | A1* | 2/2015 | Caluser | A61B 8/5207 600/440 |
| 2015/0087981 | A1 | 3/2015 | Ishii et al. | |
| 2017/0090571 | A1* | 3/2017 | Bjaerum | A61B 8/4254 |
| 2018/0246208 | A1* | 8/2018 | Dittmer | G01S 7/52084 |
| 2021/0030486 | A1* | 2/2021 | Zhang | A61B 34/20 |
| 2021/0161506 | A1* | 6/2021 | Ito | A61B 8/429 |

FOREIGN PATENT DOCUMENTS

| | | |
|---|---|---|
| JP | 5361166 | 12/2013 |
| JP | 2014014659 | 1/2014 |
| WO | 2012164892 | 12/2012 |

OTHER PUBLICATIONS

"International Search Report (Form PCT/ISA/210) of PCT/JP2020/016817," mailed on Jul. 14, 2020, with English translation thereof, pp. 1-5.

"Written Opinion of the International Searching Authority (Form PCT/ISA/237)" of PCT/JP2020/016817, mailed on Jul. 14, 2020, with English translation thereof, pp. 1-10.

\* cited by examiner

THREE-DIMENSIONAL ULTRASOUND IMAGE GENERATION APPARATUS, THREE-DIMENSIONAL ULTRASOUND IMAGE GENERATION METHOD, AND THREE-DIMENSIONAL ULTRASOUND IMAGE GENERATION PROGRAM

CROSS-REFERENCE TO RELATED APPLICATIONS

This application is a Continuation of PCT International Application No. PCT/JP2020/016817 filed on Apr. 17, 2020, which claims priority under 35 U.S.C § 119(a) to Japanese Patent Application No. 2019-106449 filed on Jun. 6, 2019. Each of the above application(s) is hereby expressly incorporated by reference, in its entirety, into the present application.

BACKGROUND OF THE INVENTION

1. Field of the Invention

The present disclosure relates to a three-dimensional ultrasound image generation apparatus, a three-dimensional ultrasound image generation method, and a three-dimensional ultrasound image generation program for generating a three-dimensional ultrasound image.

2. Description of the Related Art

In recent years, with advancements in medical apparatuses such as a computed tomography (CT) apparatus, a magnetic resonance imaging (MRI) apparatus, and an ultrasound diagnosis apparatus, image diagnosis using higher quality and higher resolution medical images has become possible. In the ultrasound diagnosis apparatus, there is known a technique of generating a three-dimensional ultrasound image from two-dimensional ultrasound images which are acquired by performing imaging by an ultrasound probe and imaging positions of the ultrasound probe. The two-dimensional ultrasound image may include an unclear image region due to an artifact caused by reflection and refraction of an ultrasound wave, a decrease in resolution of an image in proportion to a distance from the ultrasound probe, or the like. In diagnosis using the ultrasound images, for example, in a case where an imaging target is a blood vessel such as a carotid artery, a thickness of a vascular wall is measured. However, in a case where an unclear image region is included in the ultrasound image, it is difficult to measure a thickness of the vascular wall. In the related art, by imaging an observation target from different viewpoints, two-dimensional ultrasound images from different viewpoints are acquired. In this case, in the two-dimensional ultrasound images from each of the different viewpoints, by using image regions other than the unclear image region, a thickness of the vascular wall is measured.

On the other hand, in a case where a three-dimensional ultrasound image is generated using two-dimensional ultrasound images including an unclear image region, similarly, the three-dimensional ultrasound image also includes an unclear image region. Similarly, the three-dimensional ultrasound image including an unclear image region is not suitable for measuring a thickness of the vascular wall. For this reason, in recent years, there has been disclosed a technique for generating a higher-definition ultrasound image in which an unclear image region is suppressed.

JP2007-236681A discloses a method of removing an artifact by preparing a plurality of images, which have different positional relationships and include images including an artifact and images not including an artifact, and adding or subtracting pixel values of the plurality of images. In addition, JP5361166B proposes a method of suppressing image distortion due to an artifact by masking a pixel of which an angle from a normal line passing through a center of an element plane of an ultrasound probe exceeds an allowable angle and which corresponds to a scanning line by an ultrasound wave, the ultrasound probe being a device in which a plurality of ultrasound transducers are arranged. Further, JP2003-088521A discloses a method of removing or suppressing an artifact by combining images in different angle ranges in accordance with a coordinate system. Thus, even in a case where an image in one angle range includes, for example, an artifact caused by multiple reflections, when images in other angle ranges do not include an artifact, the artifact can be removed or suppressed.

SUMMARY OF THE INVENTION

However, in the techniques described in JP2007-236681A, JP5361166B, and JP2003-088521A, an organ to be measured is not extracted. As a result, in an image, it is difficult to suppress an unclear image region due to an artifact caused by an organ to be measured.

The present disclosure has been made in view of the above circumstances, and an object of the present disclosure is to generate a higher-definition three-dimensional ultrasound image by suppressing an unclear image region caused by an organ to be measured.

According to a first aspect of the present disclosure, there is provided a three-dimensional ultrasound image generation apparatus including: an image acquisition unit that acquires a plurality of two-dimensional ultrasound images from each of a first viewpoint and a second viewpoint by imaging a target organ in a subject at a plurality of imaging positions while moving an ultrasound probe in one direction along a body surface of the subject, the plurality of two-dimensional ultrasound images being acquired by performing imaging at the plurality of imaging positions from each of at least two viewpoints of the first viewpoint and the second viewpoint; a probe position information acquisition unit that acquires, for each imaging, position information including an imaging direction indicating a direction of the viewpoint of the ultrasound probe and the imaging position for each viewpoint; a three-dimensional ultrasound image generation unit that generates three-dimensional ultrasound images from each of the first viewpoint and the second viewpoint based on the plurality of two-dimensional ultrasound images from each of the first viewpoint and the second viewpoint which are acquired by the image acquisition unit and the position information for each imaging which is acquired by the probe position information acquisition unit; an organ extraction unit that extracts the organ included in the three-dimensional ultrasound images based on at least one three-dimensional ultrasound image among the three-dimensional ultrasound images from each of the first viewpoint and the second viewpoint; an image processing unit that extracts an unclear image region from the three-dimensional ultrasound image from which at least the organ is extracted among the three-dimensional ultrasound images from each of the first viewpoint and the second viewpoint, based on position information of the organ extracted by the organ extraction unit and the position information of the ultrasound probe which is acquired by the probe position information acquisition unit, and that performs suppression processing of suppressing unclearness in the extracted image region; and an image combination unit that generates a combined three-dimensional ultrasound image by combining the three-dimensional ultrasound images from two viewpoints of the first viewpoint and the second viewpoint, the three-dimensional ultrasound image on which the suppression processing is performed being included in the three-dimensional ultrasound images from at least one viewpoint among the three-dimensional ultrasound images from the two viewpoints.

According to a second aspect of the present disclosure, there is provided a three-dimensional ultrasound image generation apparatus including: an image acquisition unit that acquires a plurality of two-dimensional ultrasound images from each of a first viewpoint and a second viewpoint by imaging a target organ in a subject at a plurality of imaging positions while moving an ultrasound probe in one direction along a body surface of the subject, the plurality of two-dimensional ultrasound images being acquired by performing imaging at the plurality of imaging positions from each of at least two viewpoints of the first viewpoint and the second viewpoint; a probe position information acquisition unit that acquires, for each imaging, position information including an imaging direction indicating a direction of the viewpoint of the ultrasound probe and the imaging position for each viewpoint; an organ extraction unit that extracts the organ included in the two-dimensional ultrasound images based on at least one two-dimensional ultrasound image among the plurality of two-dimensional ultrasound images from at least one viewpoint of the first viewpoint or the second viewpoint which are acquired by the image acquisition unit; an image processing unit that extracts an unclear image region from each of the plurality of two-dimensional ultrasound images corresponding to the viewpoint of the two-dimensional ultrasound image from which at least the organ is extracted among the two-dimensional ultrasound images from each of the first viewpoint and the second viewpoint, based on position information of the organ extracted by the organ extraction unit and the position information of the ultrasound probe which is acquired by the probe position information acquisition unit, and that performs suppression processing of suppressing unclearness in the extracted image region; a three-dimensional ultrasound image generation unit that generates three-dimensional ultrasound images from two viewpoints of the first viewpoint and the second viewpoint based on each of the plurality of two-dimensional ultrasound images from two viewpoints of the first viewpoint and the second viewpoint, the two-dimensional ultrasound image on which the suppression processing is performed being included in the two-dimensional ultrasound images from at least one viewpoint among the two-dimensional ultrasound images from two viewpoints; and an image combination unit that generates a combined three-dimensional ultrasound image by combining the three-dimensional ultrasound images from two viewpoints of the first viewpoint and the second viewpoint which are generated by the three-dimensional ultrasound image generation unit.

In the present disclosure, the viewpoints may be two viewpoints or three or more viewpoints as long as the first viewpoint and the second viewpoint are included.

Further, in the three-dimensional ultrasound image generation apparatus according to the aspect of the present disclosure, the image processing unit may extract the unclear image region based on a traveling direction of an ultrasound wave emitted from the ultrasound probe to the organ, the traveling direction of the ultrasound wave being derived based on the position information of the organ extracted by the organ extraction unit and the position information of the ultrasound probe.

Further, in the three-dimensional ultrasound image generation apparatus according to the aspect of the present disclosure, the image processing unit may extract, as the unclear image region, a region in which an angle formed by the traveling direction of the ultrasound wave and an outer front surface of the organ is equal to or smaller than a predetermined threshold value.

Further, in the three-dimensional ultrasound image generation apparatus according to the aspect of the present disclosure, the suppression processing may be processing of decreasing a pixel value of the unclear image region to be relatively lower than pixel values of other regions.

Further, in the three-dimensional ultrasound image generation apparatus according to the aspect of the present disclosure, the image combination unit may perform averaging processing of averaging pixel values of pixels at the same positions based on the three-dimensional ultrasound image from two viewpoints of the first viewpoint and the second viewpoint, the averaging processing being processing of averaging the pixel values of regions other than the unclear image region on which the suppression processing is performed.

Further, the three-dimensional ultrasound image generation apparatus according to the aspect of the present disclosure may further include a display control unit that causes a display unit to display at least one image of the two-dimensional ultrasound image or the three-dimensional ultrasound image. The display control unit may control the display unit to display the combined three-dimensional ultrasound image, and may control the display unit to display the two-dimensional ultrasound images which are imaged at imaging positions closest to a position designated by a user on the combined three-dimensional ultrasound image which is displayed.

Further, the three-dimensional ultrasound image generation apparatus according to the aspect of the present disclosure may further include a marker member that is fixed to the ultrasound probe, and an image capturing unit that captures an image of the ultrasound probe and the marker member within the same image capturing range. The probe position information acquisition unit may acquire the position information of the ultrasound probe based on a captured image of the ultrasound probe and the marker member which is acquired by the image capturing unit.

Further, the three-dimensional ultrasound image generation apparatus according to the aspect of the present disclosure may further include a six-axis sensor that is provided on the ultrasound probe. The probe position information acquisition unit may acquire the position information of the ultrasound probe based on output information which is output from the six-axis sensor.

Further, the three-dimensional ultrasound image generation apparatus according to the aspect of the present disclosure may further include a marker member that is fixed to the ultrasound probe, a six-axis sensor that is provided on the ultrasound probe, and an image capturing unit that captures an image of the ultrasound probe and the marker member within the same image capturing range. The probe position information acquisition unit may acquire the position information of the ultrasound probe based on a captured image of the ultrasound probe and the marker member which is acquired by the image capturing unit and output information which is output from the six-axis sensor.

According to a first aspect of the present disclosure, there is provided a three-dimensional ultrasound image generation method including: acquiring a plurality of two-dimensional ultrasound images from each of a first viewpoint and a second viewpoint by imaging a target organ in a subject at a plurality of imaging positions while moving an ultrasound probe in one direction along a body surface of the subject, the plurality of two-dimensional ultrasound images being acquired by performing imaging at the plurality of imaging positions from each of at least two viewpoints of the first viewpoint and the second viewpoint; acquiring, for each imaging, position information including an imaging direction indicating a direction of the viewpoint of the ultrasound probe and the imaging position for each viewpoint; generating three-dimensional ultrasound images from each of the first viewpoint and the second viewpoint based on the plurality of acquired two-dimensional ultrasound images from each of the first viewpoint and the second viewpoint and the acquired position information for each imaging; extracting the organ included in the three-dimensional ultrasound images based on at least one three-dimensional ultrasound image among the three-dimensional ultrasound images from each of the first viewpoint and the second viewpoint; extracting an unclear image region from the three-dimensional ultrasound image from which at least the organ is extracted among the three-dimensional ultrasound images from each of the first viewpoint and the second viewpoint, based on position information of the extracted organ and the acquired position information of the ultrasound probe, and performing suppression processing of suppressing unclearness in the extracted image region; and generating a combined three-dimensional ultrasound image by combining the three-dimensional ultrasound images from two viewpoints of the first viewpoint and the second viewpoint, the three-dimensional ultrasound image on which the suppression processing is performed being included in the three-dimensional ultrasound images from at least one viewpoint among the three-dimensional ultrasound images from the two viewpoints.

According to a second aspect of the present disclosure, there is provided a three-dimensional ultrasound image generation method including: acquiring a plurality of two-dimensional ultrasound images from each of a first viewpoint and a second viewpoint by imaging a target organ in a subject at a plurality of imaging positions while moving an ultrasound probe in one direction along a body surface of the subject, the plurality of two-dimensional ultrasound images being acquired by performing imaging at the plurality of imaging positions from each of at least two viewpoints of the first viewpoint and the second viewpoint; acquiring, for each imaging, position information including an imaging direction indicating a direction of the viewpoint of the ultrasound probe and the imaging position for each viewpoint; extracting the organ included in the two-dimensional ultrasound images based on at least one two-dimensional ultrasound image among the plurality of acquired two-dimensional ultrasound images from at least one viewpoint of the first viewpoint or the second viewpoint; extracting an unclear image region from each of the plurality of two-dimensional ultrasound images corresponding to the viewpoint of the two-dimensional ultrasound image from which at least the organ is extracted among the two-dimensional ultrasound images from each of the first viewpoint and the second viewpoint, based on position information of the extracted organ and the acquired position information of the ultrasound probe, and performing suppression processing of suppressing unclearness in the extracted image region; generating three-dimensional ultrasound images from two viewpoints of the first viewpoint and the second viewpoint based on each of the plurality of two-dimensional ultrasound images from two viewpoints of the first viewpoint and the second viewpoint, the two-dimensional ultrasound image on which the suppression processing is performed being included in the two-dimensional ultrasound images from at least one viewpoint among the two-dimensional ultrasound images from two viewpoints; and generating a combined three-dimensional ultrasound image by combining the generated three-dimensional ultrasound images from two viewpoints of the first viewpoint and the second viewpoint.

According to a first aspect of the present disclosure, there is provided a three-dimensional ultrasound image generation program causing a computer to function as: an image acquisition unit that acquires a plurality of two-dimensional ultrasound images from each of a first viewpoint and a second viewpoint by imaging a target organ in a subject at a plurality of imaging positions while moving an ultrasound probe in one direction along a body surface of the subject, the plurality of two-dimensional ultrasound images being acquired by performing imaging at the plurality of imaging positions from each of at least two viewpoints of the first viewpoint and the second viewpoint; a probe position information acquisition unit that acquires, for each imaging, position information including an imaging direction indicating a direction of the viewpoint of the ultrasound probe and the imaging position for each viewpoint; a three-dimensional ultrasound image generation unit that generates three-dimensional ultrasound images from each of the first viewpoint and the second viewpoint based on the plurality of two-dimensional ultrasound images from each of the first viewpoint and the second viewpoint which are acquired by the image acquisition unit and the position information for each imaging which is acquired by the probe position information acquisition unit; an organ extraction unit that extracts the organ included in the three-dimensional ultrasound images based on at least one three-dimensional ultrasound image among the three-dimensional ultrasound images from each of the first viewpoint and the second viewpoint; an image processing unit that extracts an unclear image region from the three-dimensional ultrasound image from which at least the organ is extracted among the three-dimensional ultrasound images from each of the first viewpoint and the second viewpoint, based on position information of the organ extracted by the organ extraction unit and the position information of the ultrasound probe which is acquired by the probe position information acquisition unit, and that performs suppression processing of suppressing unclearness in the extracted image region; and an image combination unit that generates a combined three-dimensional ultrasound image by combining the three-dimensional ultrasound images from two viewpoints of the first viewpoint and the second viewpoint, the three-dimensional ultrasound image on which the suppression processing is performed being included in the three-dimensional ultrasound images from at least one viewpoint among the three-dimensional ultrasound images from the two viewpoints.

According to a second aspect of the present disclosure, there is provided a three-dimensional ultrasound image generation program causing a computer to function as: an image acquisition unit that acquires a plurality of two-dimensional ultrasound images from each of a first viewpoint and a second viewpoint by imaging a target organ in a subject at a plurality of imaging positions while moving an ultrasound probe in one direction along a body surface of the subject, the plurality of two-dimensional ultrasound images being acquired by performing imaging at the plurality of imaging positions from each of at least two viewpoints of the first viewpoint and the second viewpoint; a probe position information acquisition unit that acquires, for each imaging, position information including an imaging direction indicating a direction of the viewpoint of the ultrasound probe and the imaging position for each viewpoint; an organ extraction unit that extracts the organ included in the two-dimensional ultrasound images based on at least one two-dimensional ultrasound image among the plurality of two-dimensional ultrasound images from at least one viewpoint of the first viewpoint or the second viewpoint which are acquired by the image acquisition unit; an image processing unit that extracts an unclear image region from each of the plurality of two-dimensional ultrasound images corresponding to the viewpoint of the two-dimensional ultrasound image from which at least the organ is extracted among the two-dimensional ultrasound images from each of the first viewpoint and the second viewpoint, based on position information of the organ extracted by the organ extraction unit and the position information of the ultrasound probe which is acquired by the probe position information acquisition unit, and that performs suppression processing of suppressing unclearness in the extracted image region; a three-dimensional ultrasound image generation unit that generates three-dimensional ultrasound images from two viewpoints of the first viewpoint and the second viewpoint based on each of the plurality of two-dimensional ultrasound images from two viewpoints of the first viewpoint and the second viewpoint, the two-dimensional ultrasound image on which the suppression processing is performed being included in the two-dimensional ultrasound images from at least one viewpoint among the two-dimensional ultrasound images from two viewpoints; and an image combination unit that generates a combined three-dimensional ultrasound image by combining the three-dimensional ultrasound images from two viewpoints of the first viewpoint and the second viewpoint which are generated by the three-dimensional ultrasound image generation unit.

According to another first aspect of the present disclosure, there is provided a three-dimensional ultrasound image generation apparatus including: a memory that stores a command to be executed by a computer; and a processor configured to execute the stored command, in which the processor is configured to execute processing of acquiring a plurality of two-dimensional ultrasound images from each of a first viewpoint and a second viewpoint by imaging a target organ in a subject at a plurality of imaging positions while moving an ultrasound probe in one direction along a body surface of the subject, the plurality of two-dimensional ultrasound images being acquired by performing imaging at the plurality of imaging positions from each of at least two viewpoints of the first viewpoint and the second viewpoint, acquiring, for each imaging, position information including an imaging direction indicating a direction of the viewpoint of the ultrasound probe and the imaging position for each viewpoint, generating three-dimensional ultrasound images from each of the first viewpoint and the second viewpoint based on the plurality of acquired two-dimensional ultrasound images from each of the first viewpoint and the second viewpoint and the acquired position information for each imaging, extracting the organ included in the three-dimensional ultrasound images based on at least one three-dimensional ultrasound image among the three-dimensional ultrasound images from each of the first viewpoint and the second viewpoint, extracting an unclear image region from the three-dimensional ultrasound image from which at least the organ is extracted among the three-dimensional ultrasound images from each of the first viewpoint and the second viewpoint, based on position information of the extracted organ and the acquired position information of the ultrasound probe, and performing suppression processing of suppressing unclearness in the extracted image region, and generating a combined three-dimensional ultrasound image by combining the three-dimensional ultrasound images from two viewpoints of the first viewpoint and the second viewpoint, the three-dimensional ultrasound image on which the suppression processing is performed being included in the three-dimensional ultrasound images from at least one viewpoint among the three-dimensional ultrasound images from the two viewpoints.

According to another second aspect of the present disclosure, there is provided a three-dimensional ultrasound image generation apparatus including: a memory that stores a command to be executed by a computer; and a processor configured to execute the stored command, in which the processor is configured to execute processing of acquiring a plurality of two-dimensional ultrasound images from each of a first viewpoint and a second viewpoint by imaging a target organ in a subject at a plurality of imaging positions while moving an ultrasound probe in one direction along a body surface of the subject, the plurality of two-dimensional ultrasound images being acquired by performing imaging at the plurality of imaging positions from each of at least two viewpoints of the first viewpoint and the second viewpoint, acquiring, for each imaging, position information including an imaging direction indicating a direction of the viewpoint of the ultrasound probe and the imaging position for each viewpoint, extracting the organ included in the two-dimensional ultrasound images based on at least one two-dimensional ultrasound image among the plurality of acquired two-dimensional ultrasound images from at least one viewpoint of the first viewpoint or the second viewpoint, extracting an unclear image region from each of the plurality of two-dimensional ultrasound images corresponding to the viewpoint of the two-dimensional ultrasound image from which at least the organ is extracted among the two-dimensional ultrasound images from each of the first viewpoint and the second viewpoint, based on position information of the extracted organ and the acquired position information of the ultrasound probe, and performing suppression processing of suppressing unclearness in the extracted image region, generating three-dimensional ultrasound images from two viewpoints of the first viewpoint and the second viewpoint based on each of the plurality of two-dimensional ultrasound images from two viewpoints of the first viewpoint and the second viewpoint, the two-dimensional ultrasound image on which the suppression processing is performed being included in the two-dimensional ultrasound images from at least one viewpoint among the two-dimensional ultrasound images from two viewpoints, and generating a combined three-dimensional ultrasound image by combining the generated three-dimensional ultrasound images from two viewpoints of the first viewpoint and the second viewpoint.

According to the three-dimensional ultrasound image generation apparatus, the three-dimensional ultrasound image generation method, and the three-dimensional ultrasound image generation program, it is possible to generate a higher-definition three-dimensional ultrasound image by suppressing an unclear image region caused by an organ to be measured.

DESCRIPTION OF THE PREFERRED EMBODIMENTS

Figure 1:
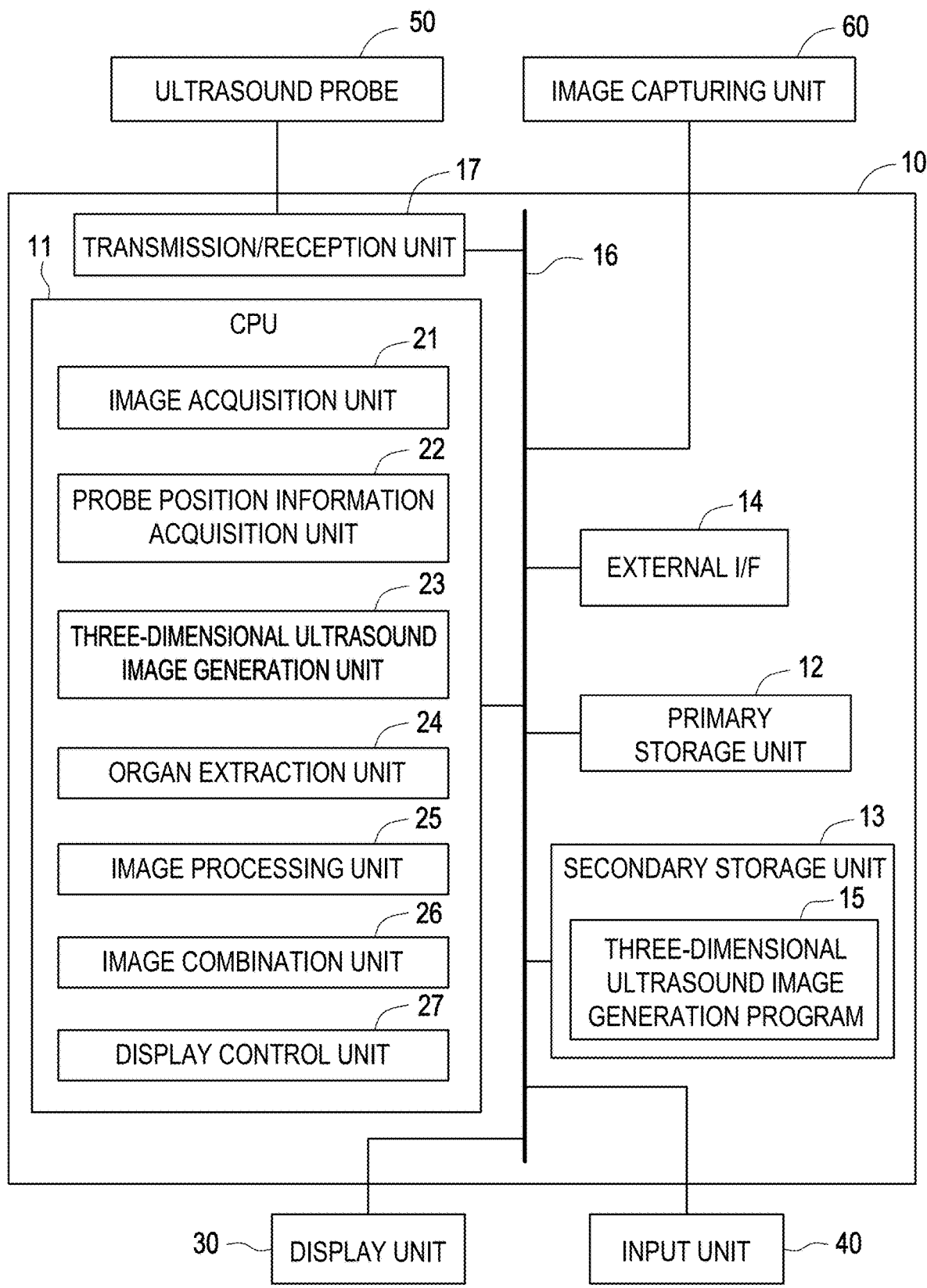
FIG. 1 is a schematic block diagram illustrating a configuration of a diagnosis support system including a three-dimensional ultrasound image generation apparatus according to a first embodiment of the present disclosure.

Hereinafter, embodiments of the present disclosure will be described with reference to the drawings. FIG. 1 is a schematic block diagram illustrating a configuration of a diagnosis support system to which a three-dimensional ultrasound image generation apparatus according to an embodiment of the present disclosure is applied. As illustrated in FIG. 1, a diagnosis support system 1 includes a three-dimensional ultrasound image generation apparatus 10 according to the present embodiment, an ultrasound probe 50 configured to be connected to the three-dimensional ultrasound image generation apparatus 10, an image capturing unit 60, a display unit 30, and an input unit 40.

The three-dimensional ultrasound image generation apparatus 10 is configured with a computer including a central processing unit (CPU) 11, a primary storage unit 12, a secondary storage unit 13, an external interface (I/F) 14, and the like. The CPU 11 controls the entire three-dimensional ultrasound image generation apparatus 10. The primary storage unit 12 is a volatile memory used as a work area or the like in execution of various programs. As an example of the primary storage unit 12, a random access memory (RAM) may be used. The secondary storage unit 13 is a non-volatile memory that stores various programs and various parameters in advance, and a three-dimensional ultrasound image generation program 15 according to an embodiment of the present disclosure is installed in the secondary storage unit 13.

The three-dimensional ultrasound image generation program 15 is distributed by being recorded on a recording medium such as a digital versatile disc (DVD) or a compact disc read only memory (CD-ROM), and is installed in a computer from the recording medium. Alternatively, the three-dimensional ultrasound image generation program 15 may be stored in a storage device of a server computer connected to a network or a network storage in a state where access from the outside is allowed, or may be downloaded and installed in a computer according to a request from the outside.

The three-dimensional ultrasound image generation program 15 is executed by the CPU 11, and thus the CPU 11 functions as an image acquisition unit 21, a probe position information acquisition unit 22, a three-dimensional ultrasound image generation unit 23, an organ extraction unit 24, an image processing unit 25, an image combination unit 26, and a display control unit 27. Examples of the secondary storage unit 13 include an electrically erasable programmable read-only memory (EEPROM), a flash memory, and the like.

The external I/F 14 controls transmission and reception of various information between the three-dimensional ultrasound image generation apparatus 10 and an external apparatus (not illustrated). The CPU 11, the primary storage unit 12, the secondary storage unit 13, and the external I/F 14 are connected to a bus line 16 which is a common route through which each circuit exchanges data.

The display unit 30 and the input unit 40 are also connected to the bus line 16. The display unit 30 is configured with, for example, a liquid crystal display or the like. As will be described later, the display unit 30 displays a two-dimensional ultrasound image acquired by the image acquisition unit 21 and a three-dimensional ultrasound image generated by the three-dimensional ultrasound image generation unit 23. Further, the display unit 30 displays a captured image acquired by the image capturing unit 60 to be described. The display unit 30 may be configured with a touch panel such that the display unit 30 also serves as the input unit 40. The input unit 40 includes a mouse and a keyboard, and receives various setting input by a user. Further, a transmission/reception unit 17 and the image capturing unit 60 such as camera are also connected to the bus line 16. The transmission/reception unit 17 controls transmission and reception of various information to and from the ultrasound probe 50 to be described.

Figure 2:
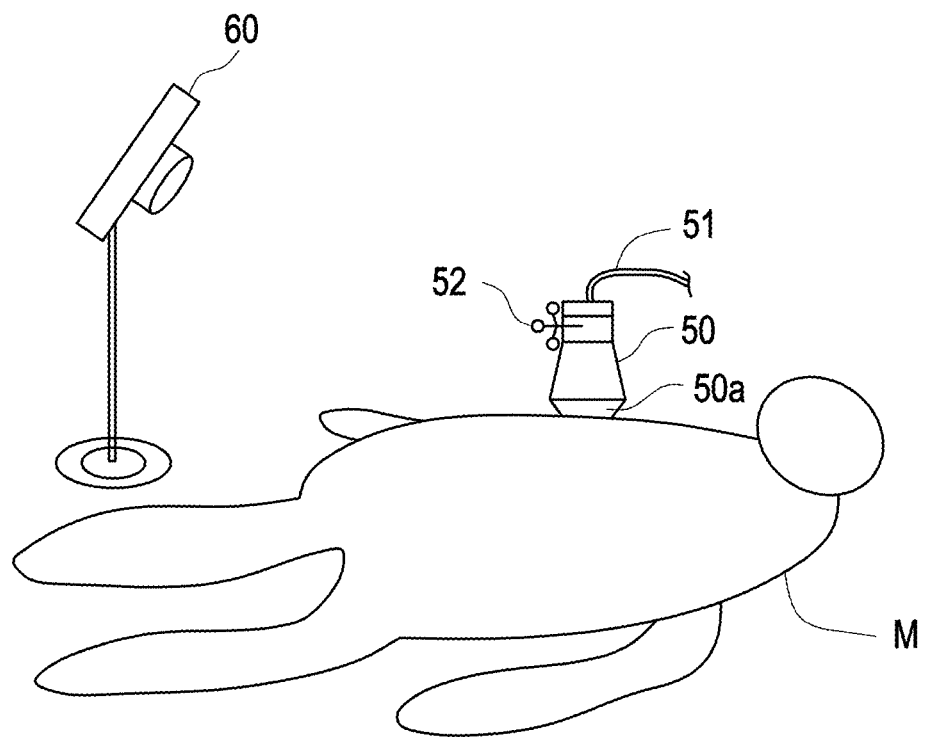
FIG. 2 is a conceptual diagram of the diagnosis support system according to an embodiment of the present disclosure.

The ultrasound probe 50 is configured to be connected to the three-dimensional ultrasound image generation apparatus 10. As the ultrasound probe 50, for example, a probe for sector scanning, a probe for linear scanning, a probe for convex scanning, and the like may be used. FIG. 2 is a conceptual diagram of the diagnosis support system according to the embodiment of the present disclosure. As illustrated in FIG. 2, the ultrasound probe 50 includes a transducer array 50a which is provided at a distal end and in which a plurality of ultrasound transducers (not illustrated) are arranged in a one-dimensional direction. In the embodiment, an example in which the transducer array 50a includes a plurality of ultrasound transducers one-dimensionally arranged is described. On the other hand, the present disclosure is not limited thereto. In the transducer array 50a, a plurality of ultrasound transducers may be two-dimensionally arranged.

In a state where the transducer array 50a is brought into contact with a body surface of a subject M as a living body, the ultrasound probe 50 emits (transmits) an ultrasound wave to a portion of the subject M to be measured, and detects (receives) the reflected ultrasound wave which is reflected and returned by the subject M. The ultrasound probe 50 converts an electric signal with a pulse wave or a continuous wave that is output from the transmission/reception unit 17 into an ultrasound wave, and emits the converted ultrasound wave. Further, the ultrasound probe 50 converts the reflected ultrasound wave that is received into an electric signal, and transmits the converted electric signal to the transmission/reception unit 17.

The transmission/reception unit 17 transmits, to the ultrasound probe 50, an electric signal with a pulse wave or a continuous wave that is for driving the plurality of ultrasound transducers included in the ultrasound probe 50. Further, the transmission/reception unit 17 receives a plurality of electric signals generated by the plurality of ultrasound transducers that receive the reflected ultrasound wave. The transmission/reception unit generates a reception signal by performing amplification and analog/digital (A/D) conversion on the received electric signal. The reception signal is, for example, a signal including a plurality of signals that are arranged in an arrangement direction of the ultrasound transducers and in a direction which is a transmission direction of the ultrasound wave and which is perpendicular to the arrangement direction of the ultrasound transducers (hereinafter, referred to as a depth direction). Each signal of the plurality of signals is a digital signal which represents, as a digital value, an amplitude of the reflected ultrasound wave. The transmission processing and the reception processing are repeatedly and continuously performed, and thus a plurality of pieces of frame data including a plurality of reception signals are generated.

In the present disclosure, the frame data refers to group data of the reception signals required to configure one tomographic image, a signal which is processed to configure tomographic image data based on the group data, or one piece of tomographic image data or a tomographic image which is configured based on the group data. In the present embodiment, the frame data refers to one piece of tomographic image data. The configured tomographic image data is stored in the primary storage unit 12.

Figure 3:
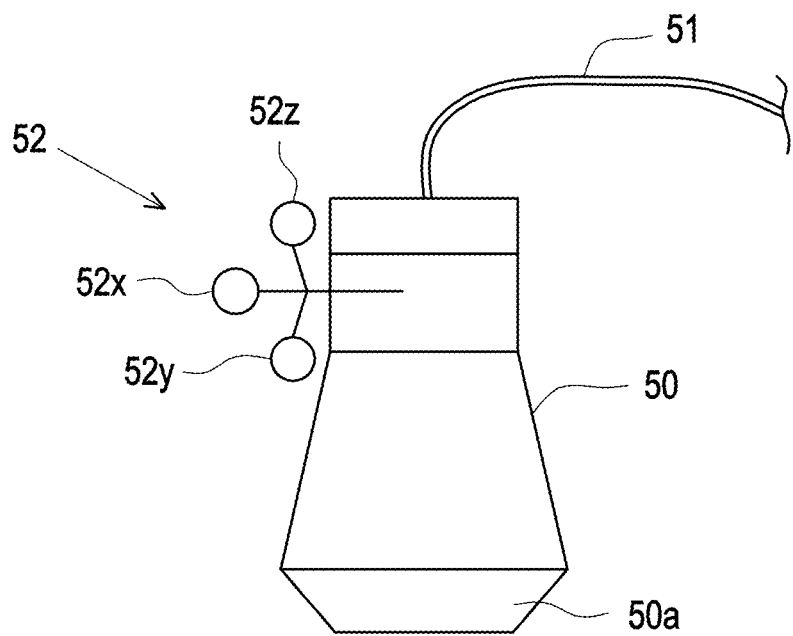
FIG. 3 is a diagram for explaining an ultrasound probe to which a marker member is fixed.

Further, in the present embodiment, a marker member is fixed to the ultrasound probe 50. FIG. 3 is a diagram for explaining the ultrasound probe 50 to which a marker member is fixed according to an embodiment of the present disclosure. In FIG. 3, a portion at which the marker member is fixed to the ultrasound probe 50 is simply illustrated, unlike an actual shape.

As illustrated in FIG. 3, the ultrasound probe 50 includes a cable 51 for connection with the transmission/reception unit 17. Further, a marker member 52 is fixed to an outer circumferential surface of the ultrasound probe 50. The marker member 52 includes three spherical markers, that is, a marker 52x, a marker 52y, and a marker 52z, and three axes of an x-axis, a y-axis, and a z-axis of which axial directions are orthogonal to each other. The three markers of the marker 52x, the marker 52y, and the marker 52z are respectively provided at one ends of the three axes of the x-axis, the y-axis, and the z-axis, with a marker center 52a as a center of the markers. The other ends of the three axes of the x-axis, the y-axis, and the z-axis are provided on a column provided on the ultrasound probe 50. Further, the three markers of the marker 52x, the marker 52y, and the marker 52z are colored, for example, in different colors, and can be identified by the colors.

In the present embodiment, a configuration in which the marker member 52 includes the three markers of the marker 52x, the marker 52y, and the marker 52z is described. On the other hand, the technique of the present disclosure is not limited thereto, and markers other than the three markers may be used. For example, four or five markers may be used. Further, the shape of the marker is not limited to a spherical shape, and may be, for example, a rectangular parallelepiped shape or a conical shape, and may be appropriately changed.

Figure 4:
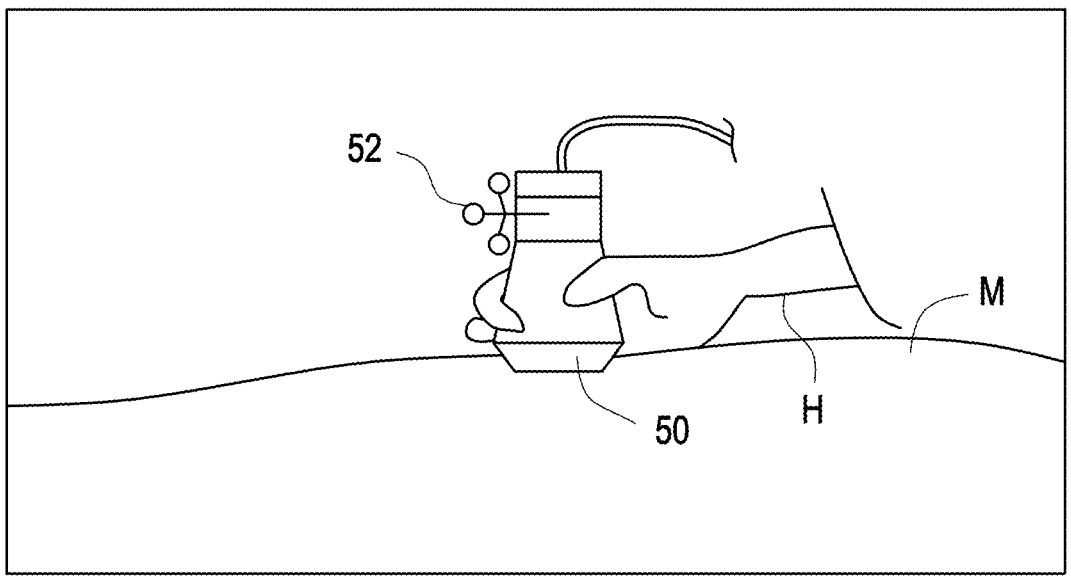
FIG. 4 is a diagram illustrating an example of an image acquired by an image capturing unit.

The image capturing unit 60 illustrated in FIG. 2 is provided at a position at which the ultrasound probe 50 and the marker member 52 can be captured together within the same image capturing range. FIG. 4 is a diagram illustrating an example of an image acquired by the image capturing unit 60. As illustrated in FIG. 4, in an image D acquired by the image capturing unit 60, the ultrasound probe 50 that is held by a hand H of the user and that is brought into contact with a body surface of the subject M and the marker member 52 that is fixed to the ultrasound probe 50 appear.

Figure 5:
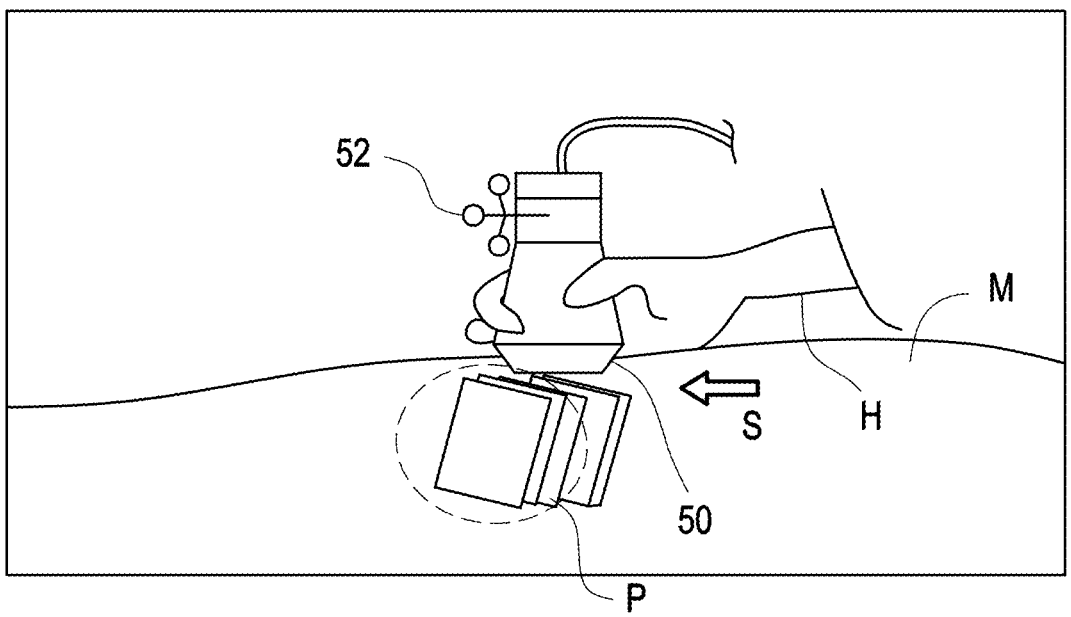
FIG. 5 is a diagram for explaining an imaging operation by the ultrasound probe.

FIG. 5 is a diagram for explaining an imaging operation by the ultrasound probe 50. As illustrated in FIG. 5, in a state where the ultrasound probe 50 is brought into contact with the body surface of the subject M by the user, imaging is performed at different positions by moving the ultrasound probe 50 in a direction indicated by, for example, an arrow S. A plurality of two-dimensional ultrasound images P are acquired at a plurality of different imaging positions at which imaging is performed. The imaging position is a position of the ultrasound probe 50 on the body surface for each imaging. The two-dimensional ultrasound image P is a tomographic image having a cross section extending in a depth direction from each imaging position to the inside of the subject.

Figure 6:
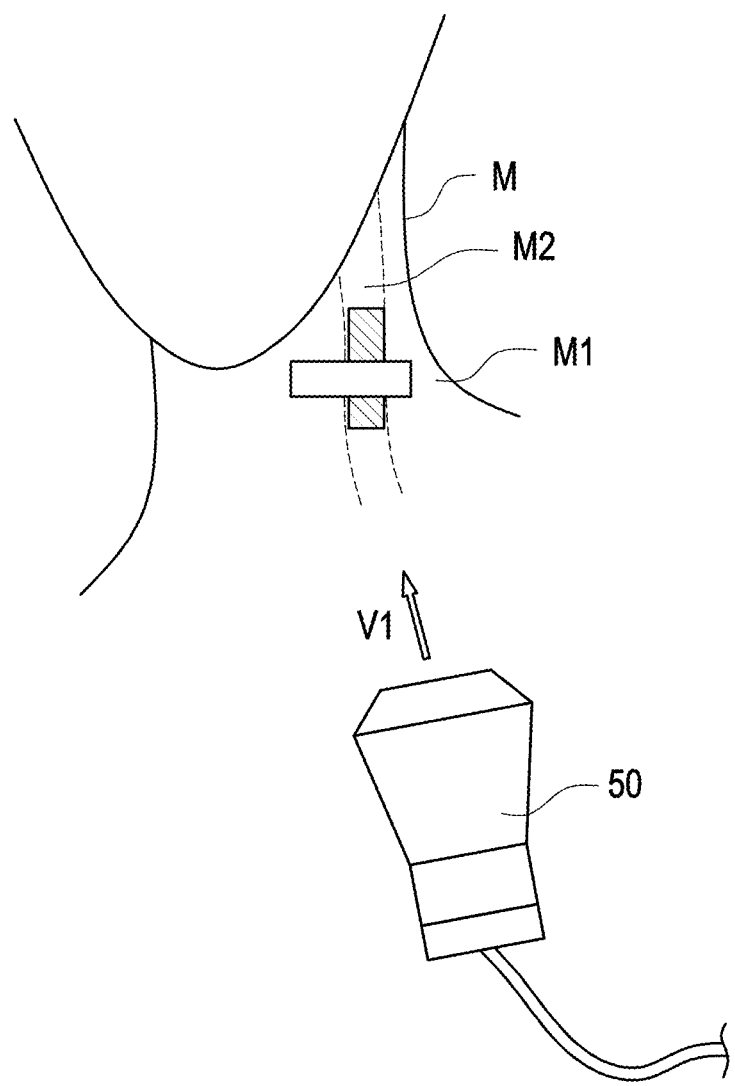
FIG. 6 is a diagram for explaining imaging of an organ in a subject from different viewpoints.
Figure 7:
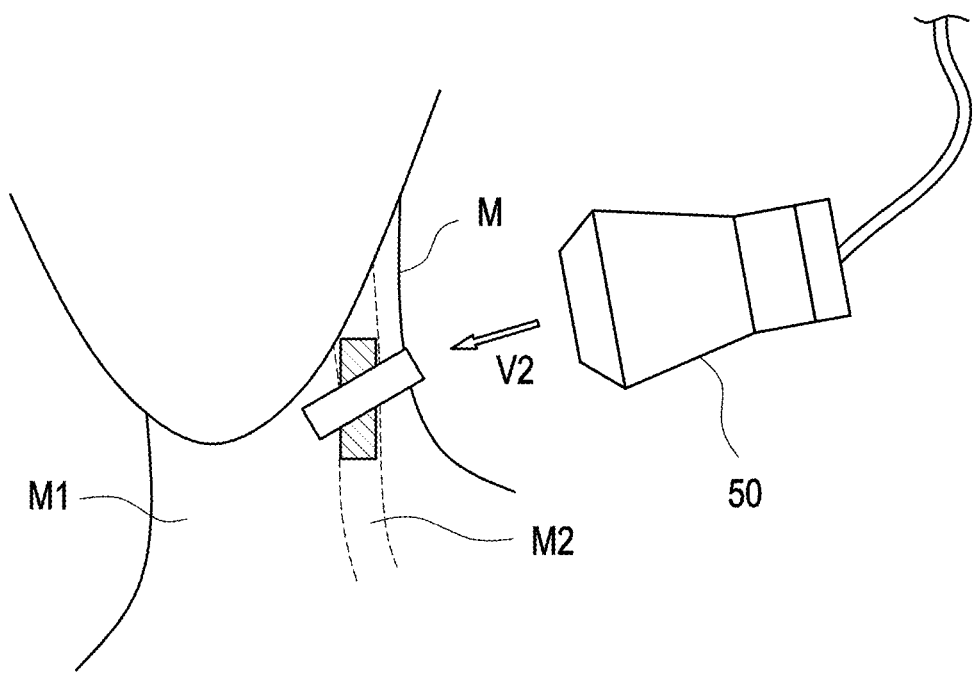
FIG. 7 is a diagram for explaining imaging of an organ in a subject from different viewpoints.

FIG. 6 and FIG. 7 are diagrams for explaining imaging of an organ in the subject from different viewpoints. In the present embodiment, as an organ in the subject M, a blood vessel, specifically, a carotid artery M2, is imaged. As illustrated in FIG. 6, in a state where the ultrasound probe 50 is brought into contact with a cervical portion M1 of the subject M from a front surface side of the subject M (a direction of an arrow V1), the ultrasound probe 50 is moved along the carotid artery M2 by the user. Thereby, the carotid artery M2 is imaged at a plurality of imaging positions. At this time, the ultrasound probe 50 is brought into contact with the cervical portion M1 such that the arrangement direction of the ultrasound transducers of the ultrasound probe 50 is orthogonal to the carotid artery M2 and a blood flow direction, that is, in a direction indicated by a black region in FIG. 6. Thereby, a minor-axis cross section of a blood vessel in a minor-axis direction of the carotid artery is imaged. Further, the ultrasound probe 50 is brought into contact with the cervical portion M1 such that the arrangement direction of the ultrasound transducers of the ultrasound probe 50 matches with the carotid artery M2 and a blood flow direction, that is, in a direction indicated by a shaded region in FIG. 6. Thereby, a major-axis cross section of a blood vessel in a major-axis direction of the carotid artery is imaged. Here, the arrow V1 of the present embodiment corresponds to a first viewpoint of the present disclosure.

Further, as illustrated in FIG. 7, in a state where the ultrasound probe 50 is brought into contact with the cervical portion M1 of the subject M from a left side of the subject M (a direction of an arrow V2), the ultrasound probe 50 is moved along the carotid artery M2 by the user. Thereby, the carotid artery M2 is imaged at a plurality of imaging positions. At this time, the ultrasound probe 50 is brought into contact with the cervical portion M1 such that the arrangement direction of the ultrasound transducers of the ultrasound probe 50 is orthogonal to the carotid artery M2 and a blood flow direction, that is, in a direction indicated by a black region in FIG. 7. Thereby, a minor-axis cross section of a blood vessel in a minor-axis direction of the carotid artery is imaged. Further, the ultrasound probe 50 is brought into contact with the cervical portion M1 such that the arrangement direction of the ultrasound transducers of the ultrasound probe 50 matches with the carotid artery M2 and a blood flow direction, that is, in a direction indicated by a shaded region in FIG. 7. Thereby, a major-axis cross section of a blood vessel in a major-axis direction of the carotid artery is imaged. Here, the arrow V2 of the present embodiment corresponds to a second viewpoint of the present disclosure.

Returning to FIG. 2, the image acquisition unit 21 acquires two-dimensional ultrasound images P which are imaged by the ultrasound probe 50 at a plurality of imaging positions from at least two viewpoints including the first viewpoint and the second viewpoint. The two-dimensional ultrasound image P is a tomographic image having a cross section extending in a depth direction from each imaging position to the inside of the subject. The ultrasound probe 50 outputs, to the primary storage unit 12, the plurality of two-dimensional ultrasound images P (tomographic images) which are imaged. The image acquisition unit 21 acquires the two-dimensional ultrasound images P (tomographic images) from the primary storage unit 12.

In each imaging, the probe position information acquisition unit 22 acquires position information including an imaging direction indicating a direction of the viewpoint of the ultrasound probe 50 and an imaging position for each viewpoint. Specifically, at each of different imaging positions, the image capturing unit 60 captures the ultrasound probe 50 and the marker member 52. A captured image which is obtained by capturing the ultrasound probe 50 and the marker member 52 is output to the primary storage unit 12. The probe position information acquisition unit 22 reads the captured image from the primary storage unit 12. The probe position information acquisition unit 22 derives position information including the imaging direction and the imaging position of the ultrasound probe 50, from a position of a marker center 52a, and positions, sizes, and inclinations of the markers 52x, 52y, and 52z in the captured image, by performing image analysis on the captured image which is read. The probe position information acquisition unit 22 identifies each of the markers 52x, 52y, and 52z by color. The probe position information acquisition unit 22 acquires position information including the imaging direction and the imaging position via derivation processing.

Figure 8:
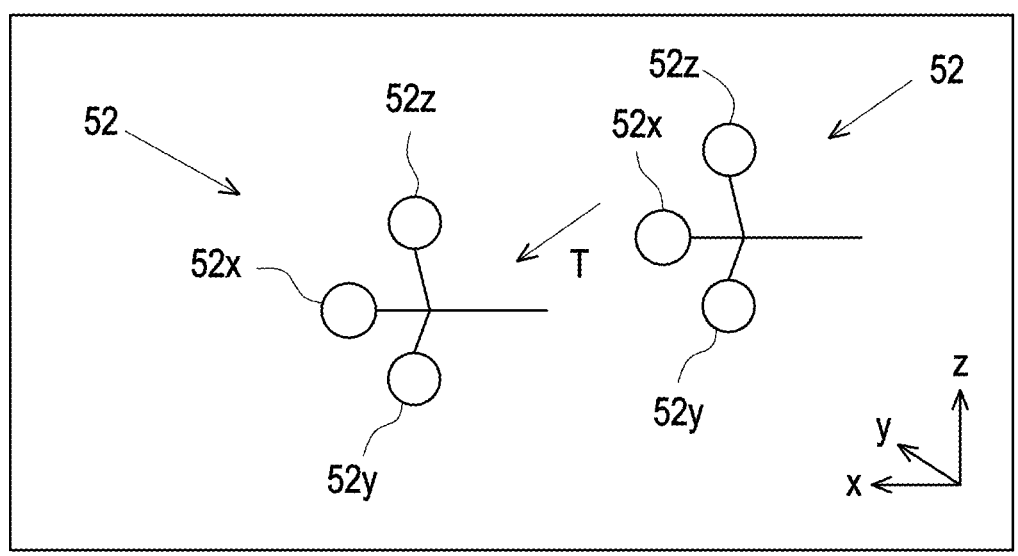
FIG. 8 is a diagram for explaining movement of the marker member 52 in a captured image.

FIG. 8 is a diagram for explaining movement of the marker member 52 in the captured image. In a case where the ultrasound probe 50 acquires the two-dimensional ultrasound images P at an imaging position T1 and an imaging position T2, for example, as illustrated in FIG. 8, the marker member 52 moves in a direction of an arrow T in the captured image. In this case, a position of the ultrasound probe 50 in an x direction is derived from an amount of movement of the marker center 52a in the x direction. In addition, a position of the ultrasound probe 50 in a y direction is derived from an amount of change in the sizes of the markers 52x, 52y, and 52z. Further, an amount of rotation of the marker member 52 is detected from a movement trajectory of the marker center 52a of the markers 52x, 52y, and 52z. The direction of the ultrasound probe 50, that is, the imaging direction, is derived based on the amount of rotation. The derived position information including the imaging position and the imaging direction of the ultrasound probe 50 is stored in the primary storage unit 12 by being associated with the two-dimensional ultrasound image P which is acquired at the imaging position. As a method of acquiring the imaging direction and the imaging position of the ultrasound probe 50 using the marker member 52, a known technique may be used.

The three-dimensional ultrasound image generation unit 23 generates a three-dimensional ultrasound image V for a space determined by an angle range or a stroke of mechanical scanning of the transducer array 50a and an electronic scanning range of the transducer array 50a, by using the two-dimensional ultrasound image P acquired by the image acquisition unit 21 and the position information that is stored in the primary storage unit 12 by being associated with the two-dimensional ultrasound image P and that includes the imaging direction and the imaging position of the ultrasound probe 50. As a method of generating the three-dimensional ultrasound image V, a known technique may be used.

The organ extraction unit 24 extracts at least one organ included in the two-dimensional ultrasound image P or the three-dimensional ultrasound image V, based on the two-dimensional ultrasound image P acquired by the image acquisition unit 21 or the three-dimensional ultrasound image V generated by the three-dimensional ultrasound image generation unit 23. Here, the organ is not limited to a visceral region such as a heart and a liver. On the other hand, the organ may also include a bone and a blood vessel.

In the present embodiment, an imaging target is a cervical portion. For this reason, the organ extraction unit 24 extracts, as a target, a blood vessel in the three-dimensional ultrasound image V. As a method of extracting a blood vessel, for example, a method described in JP2010-220742A may be used, the method being a method of obtaining position information and a main axial direction of a plurality of candidate points representing a target tissue having a linear structure and performing reconfiguration such that the plurality of candidate points are connected by using a cost function having variables based on the obtained position information and the obtained main axial direction. Alternatively, a method which is described in JP2011-212314A and automatically distinguishes and extracts a blood vessel may be used.

Further, a neural network may be used, the neural network being trained by using, as training data, the two-dimensional ultrasound image P, the three-dimensional ultrasound image V, and correct answer data of various organs so as to output a region representing an organ in a case where the two-dimensional ultrasound image P or the three-dimensional ultrasound image V is input.

The image processing unit 25 performs suppression processing of extracting, based on the position information of the organ extracted by the organ extraction unit 24 and the position information of the ultrasound probe 50 acquired by the probe position information acquisition unit 22, an unclear image region from the two-dimensional ultrasound image P and the three-dimensional ultrasound image V from which an organ is extracted, and suppressing unclearness in the extracted image region.

Figure 9:
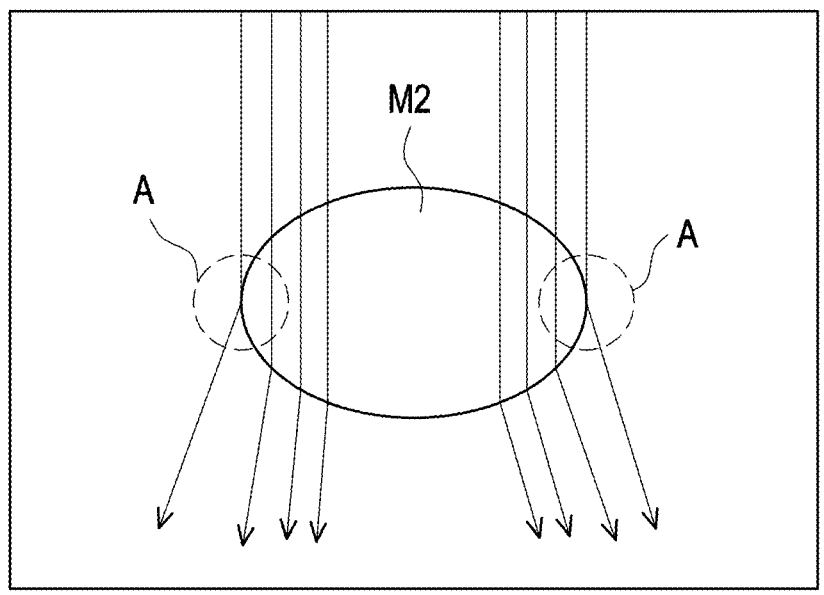
FIG. 9 is a diagram for explaining an unclear image region.

The image processing unit 25 extracts an unclear image region based on a traveling direction of the ultrasound wave emitted from the ultrasound probe 50 to the organ. First, a case where the organ extraction unit 24 extracts an organ based on the three-dimensional ultrasound image V generated by the three-dimensional ultrasound image generation unit 23 will be described. FIG. 9 illustrates a diagram for explaining an unclear image region. For convenience of explanation, FIG. 9 illustrates a minor-axis cross section of a blood vessel in a minor-axis direction of the carotid artery M2, that is, a two-dimensional ultrasound image P. On the other hand, the same explanation may be given for a three-dimensional ultrasound image V.

As illustrated in FIG. 9, in a round-shaped organ such as a blood vessel of the carotid artery M2, the ultrasound wave is reflected or refracted on an outer front surface of the organ, specifically, in the vicinity of a dotted circle indicated by A of FIG. 9. As a result, an artifact is likely to occur. For this reason, the image processing unit 25 performs suppression processing of suppressing unclearness in a region which is an unclear image region and in which an artifact is likely to occur.

Figure 10:
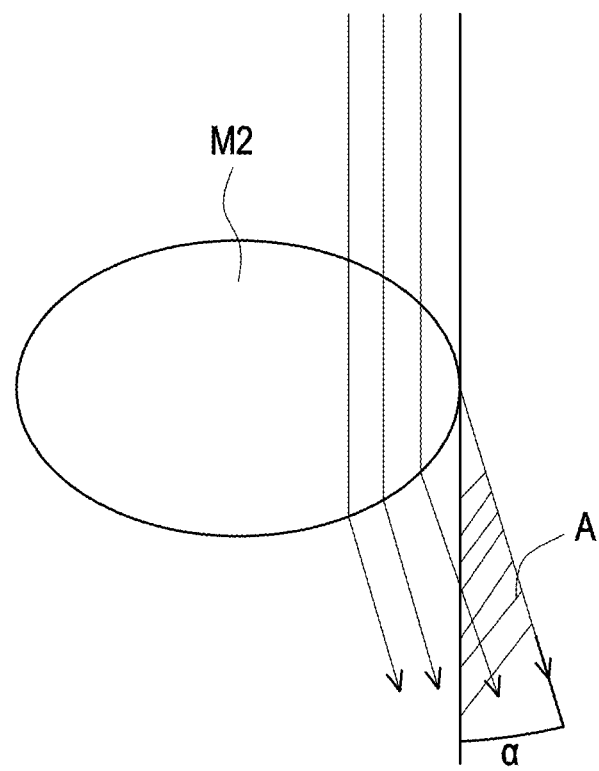
FIG. 10 is a diagram for explaining suppression processing.

FIG. 10 is a diagram for explaining suppression processing. In the present embodiment, as illustrated in FIG. 10, the image processing unit 25 extracts, as an unclear image region, a region in which an angle α formed by the traveling direction of the ultrasound wave and the outer front surface of the carotid artery M2 is equal to or smaller than a predetermined threshold value. Specifically, in FIG. 10, as an unclear image region, a region between the traveling direction of the ultrasound wave indicated by an arrow and the outer front surface of the carotid artery M2 (in FIG. 10, a region indicated by a shaded region) is extracted. Here, the angle α is a value which is calculated for each of sizes and types of organs based on a relationship between an angle measured in advance and an artifact.

Figure 11:
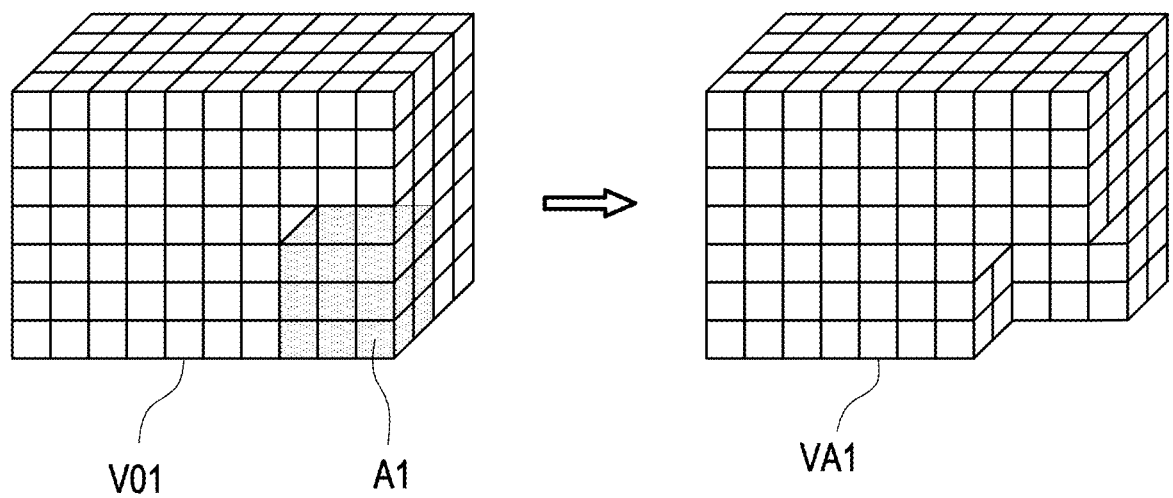
FIG. 11 is a diagram for explaining an unclear image region in a three-dimensional ultrasound image from a first viewpoint.

FIG. 11 is a diagram for explaining an unclear image region in a three-dimensional ultrasound image VO1 from the first viewpoint. In FIG. 11, for convenience of explanation, one unclear image region will be described below. On the other hand, the same explanation may be given even in a case where there are two or more unclear image regions. As illustrated in a left part of FIG. 11, in the three-dimensional ultrasound image VO1 from the first viewpoint, in a case where the image processing unit 25 extracts an unclear image region A1, as illustrated in a right part of FIG. 11, the image processing unit 25 performs processing of deleting the unclear image region A1, and performs the suppression processing on an image from which the unclear image region A1 is deleted. Thereby, a three-dimensional ultrasound image VA1 from the first viewpoint is generated.

Next, a case where the organ extraction unit 24 extracts an organ based on the plurality of two-dimensional ultrasound images P acquired by the image acquisition unit 21 will be described. Even in a case of the two-dimensional ultrasound images P, similar to the above-described three-dimensional ultrasound image V, as illustrated in FIG. 9, in a round-shaped organ such as a blood vessel of the carotid artery M2, the ultrasound wave is reflected or refracted on an outer front surface of the organ, specifically, in the vicinity of a dotted circle indicated by A of FIG. 9. As a result, an artifact is likely to occur. For this reason, the image processing unit 25 performs suppression processing of suppressing unclearness in a region which is an unclear image region and in which an artifact is likely to occur. Specifically, similar to the case of the three-dimensional ultrasound image V, as illustrated in FIG. 10, the image processing unit 25 extracts, as an unclear image region, a region in which an angle α formed by the traveling direction of the ultrasound wave and the outer front surface of the carotid artery M2 is equal to or smaller than a predetermined threshold value.

Figure 12:
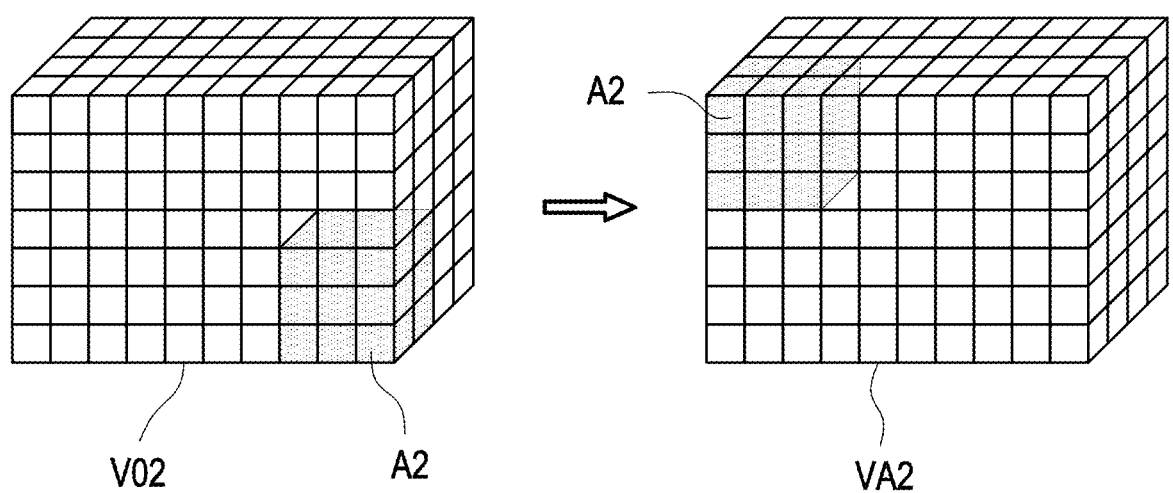
FIG. 12 is a diagram for explaining processing on a three-dimensional ultrasound image from a second viewpoint.

The image combination unit 26 generates a combined three-dimensional ultrasound image VG by combining the three-dimensional ultrasound image VA1 after the suppression processing from the first viewpoint with a three-dimensional ultrasound image VO2 from a second viewpoint. FIG. 12 is a diagram for explaining processing on the three-dimensional ultrasound image VO2 from the second viewpoint. The three-dimensional ultrasound image VO2 from the second viewpoint is an image that is imaged in an imaging direction different from the imaging direction in the first viewpoint. Thus, on the outer front surface of the carotid artery M2 irradiated with the ultrasound wave, a position from the second viewpoint is different from a position from the first viewpoint. Therefore, as illustrated in FIG. 12, in the three-dimensional ultrasound image VO2 from the second viewpoint, a region in which an artifact occurs, that is, an unclear image region A2, is at a position different from a position of the unclear image region A1 of FIG. 11.

The image combination unit 26 performs alignment processing of the carotid artery M2 included in the three-dimensional ultrasound image VO1 from the first viewpoint and the carotid artery M2 included in the three-dimensional ultrasound image VO2 from the second viewpoint. In the present embodiment, as illustrated in a right part of FIG. 12, the alignment processing is performed on the three-dimensional ultrasound image VO2 from the second viewpoint, and thus a three-dimensional ultrasound image VA2 after the alignment processing from the second viewpoint on which the alignment processing is performed is generated. The alignment processing may be performed on the three-dimensional ultrasound image VO1 from the first viewpoint, or may be performed on both of the three-dimensional ultrasound image VO1 from the first viewpoint and the three-dimensional ultrasound image VO2 from the second viewpoint. A known technique can be used for the alignment processing.

Figure 13:
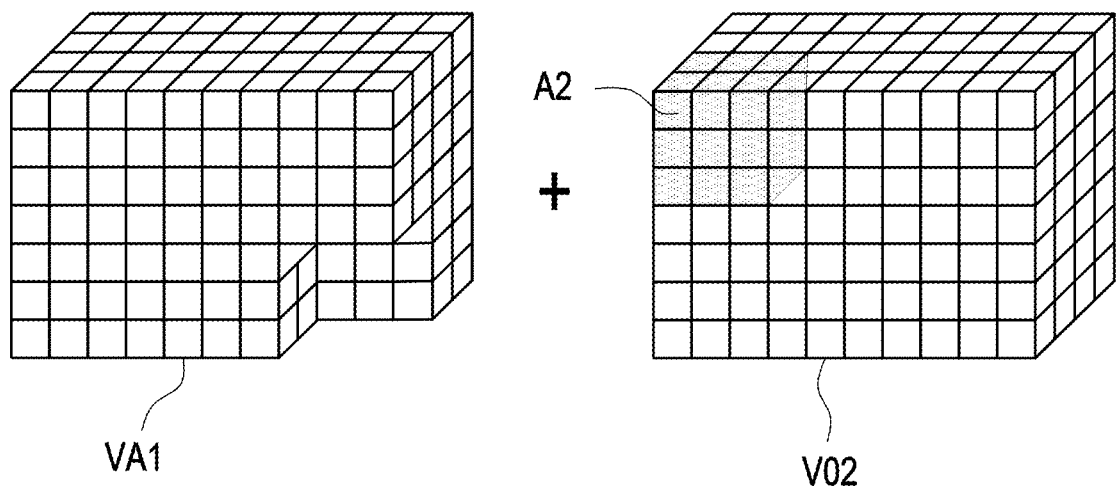
FIG. 13 is a diagram for explaining combination processing.
Figure 14:
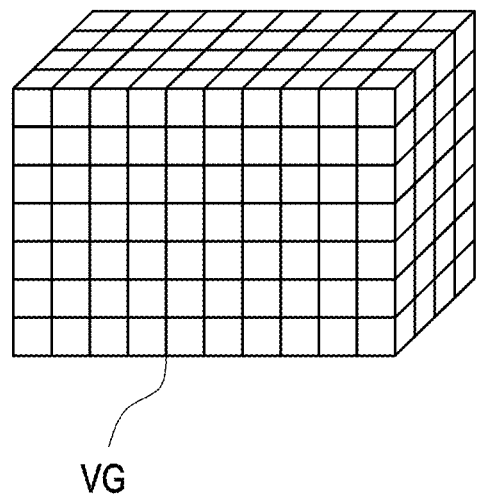
FIG. 14 is a diagram for explaining a combined three-dimensional ultrasound image VG.

FIG. 13 is a diagram for explaining combination processing. As illustrated in FIG. 13, the image combination unit 26 combines a region in the three-dimensional ultrasound image VA1 after the suppression processing from the first viewpoint from which the unclear image region A1 is deleted with a region in the three-dimensional ultrasound image VA2 after the alignment processing from the second viewpoint that corresponds to the deleted region. FIG. 14 is a diagram for explaining a combined three-dimensional ultrasound image VG. In the three-dimensional ultrasound image VA1 after the suppression processing from the first viewpoint, the unclear image region A1 is deleted. Thus, the unclear image region does not exist. The three-dimensional ultrasound image VA1 after the suppression processing from the first viewpoint from which the unclear image region is deleted is combined with the region other than the unclear image region A2 in the three-dimensional ultrasound image VA2 after the alignment processing from the second viewpoint. Thereby, a combined three-dimensional ultrasound image VG after the combination processing does not include an unclear image region, and is a three-dimensional ultrasound image with definition higher than that of the three-dimensional ultrasound image VO1 from the first viewpoint.

Returning to FIG. 2, the display control unit 27 causes the display unit 30 to display at least one of the two-dimensional ultrasound image P which is imaged by the ultrasound probe 50 or the three-dimensional ultrasound image V. Further, the display control unit 27 causes the display unit 30 to display the combined three-dimensional ultrasound image VG which is combined by the image combination unit 26. The display control unit 27 may cause one display unit 30 to display at least one of the two-dimensional ultrasound image P which is imaged by the ultrasound probe 50, the three-dimensional ultrasound image V, or the combined three-dimensional ultrasound image VG. In a case where there are two display units 30, each display unit may display the ultrasound images.

Figure 15:
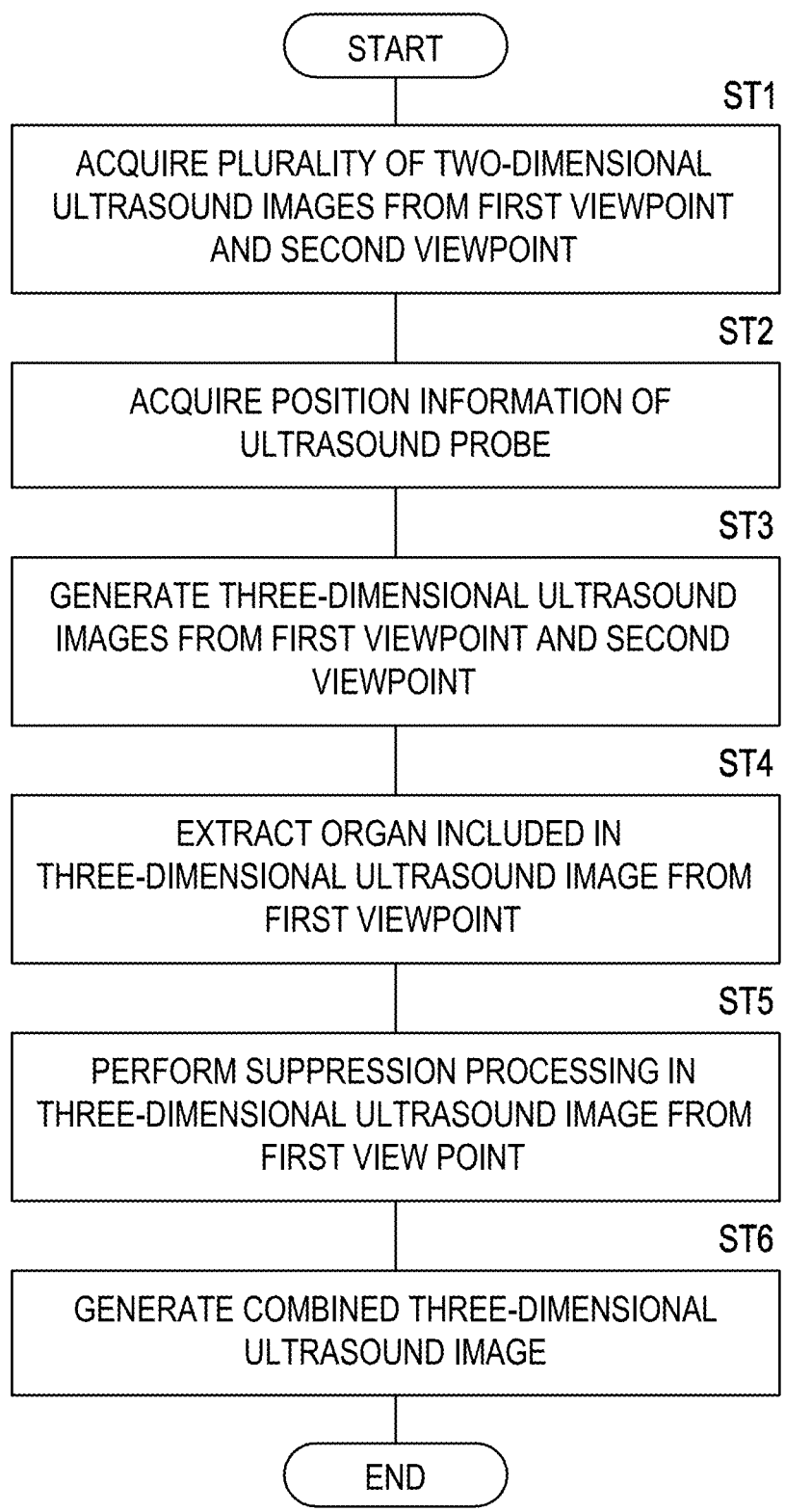
FIG. 15 is a flowchart illustrating processing performed in the first embodiment of the present disclosure.

Next, processing performed in the present embodiment will be described. FIG. 15 is a flowchart illustrating processing performed in a first embodiment of the present disclosure.

In a case where the user operates the ultrasound probe 50 in a state where the ultrasound probe 50 is brought into contact with the body surface of the cervical portion M1 of the subject M, the image acquisition unit 21 acquires a plurality of two-dimensional ultrasound images P that are imaged from a first viewpoint and a second viewpoint which are different viewpoints (step ST1).

The probe position information acquisition unit 22 acquires, for each imaging in step ST1, position information including an imaging direction indicating a direction of the viewpoint of the ultrasound probe 50 and an imaging position for each viewpoint (step ST2). The three-dimensional ultrasound image generation unit 23 generates three-dimensional ultrasound images VO1 and VO2 from a first viewpoint and a second viewpoint (step ST3).

Next, the organ extraction unit 24 extracts a carotid artery M2 included in the three-dimensional ultrasound image VO1 from the first viewpoint (step ST4). The image processing unit 25 extracts an unclear image region in the three-dimensional ultrasound image VO1 from the first viewpoint, and performs suppression processing of deleting the extracted unclear image region (step ST5).

Next, the image combination unit 26 generates a combined three-dimensional ultrasound image VG (step ST6) by combining the three-dimensional ultrasound image VA1 after the suppression processing from the first viewpoint from which the unclear image region is deleted with the region other than the unclear image region A2 in the three-dimensional ultrasound image VA2 after the alignment processing from the second viewpoint. Thereafter, the process is ended.

As described above, in the present embodiment, the three-dimensional ultrasound image VA1 after the suppression processing from the first viewpoint from which the unclear image region is deleted is combined with the region other than the unclear image region A2 in the three-dimensional ultrasound image VA2 after the alignment processing from the second viewpoint. Thereby, it is possible to generate a three-dimensional ultrasound image in which an unclear image region is suppressed and which has definition higher than that of the three-dimensional ultrasound image VO1 from the first viewpoint.

In the first embodiment, the plurality of two-dimensional ultrasound images P from the first viewpoint and the second viewpoint are acquired, and the three-dimensional ultrasound images V from the first viewpoint and the second viewpoint are generated. On the other hand, the technique of the present disclosure is not limited thereto. A plurality of two-dimensional ultrasound images P from three or more viewpoints may be acquired, and three-dimensional ultrasound images V from the first viewpoint and the second viewpoint may be generated. In this case, the suppression processing of suppressing unclearness in an unclear image region may be performed only in the three-dimensional ultrasound image V from the first viewpoint, the suppression processing may be performed in the three-dimensional ultrasound images V from two or more viewpoints, or the suppression processing may be performed in the three-dimensional ultrasound images V from all viewpoints.

Further, in the first embodiment, the organ extraction unit 24 can extract an organ in both of the two-dimensional ultrasound image P and the three-dimensional ultrasound image V. On the other hand, the technique of the present disclosure is not limited thereto. In a case where an organ is extracted only in the three-dimensional ultrasound image V as in the first embodiment, the organ extraction unit 24 may not have a function of extracting an organ in the two-dimensional ultrasound image P.

Further, in the first embodiment, the organ extraction unit 24 extracts an organ in the three-dimensional ultrasound image V. On the other hand, the organ extraction unit 24 may extract an organ in the two-dimensional ultrasound image P. In this case, the image processing unit 25 performs the suppression processing on the two-dimensional ultrasound image P.

Figure 16:
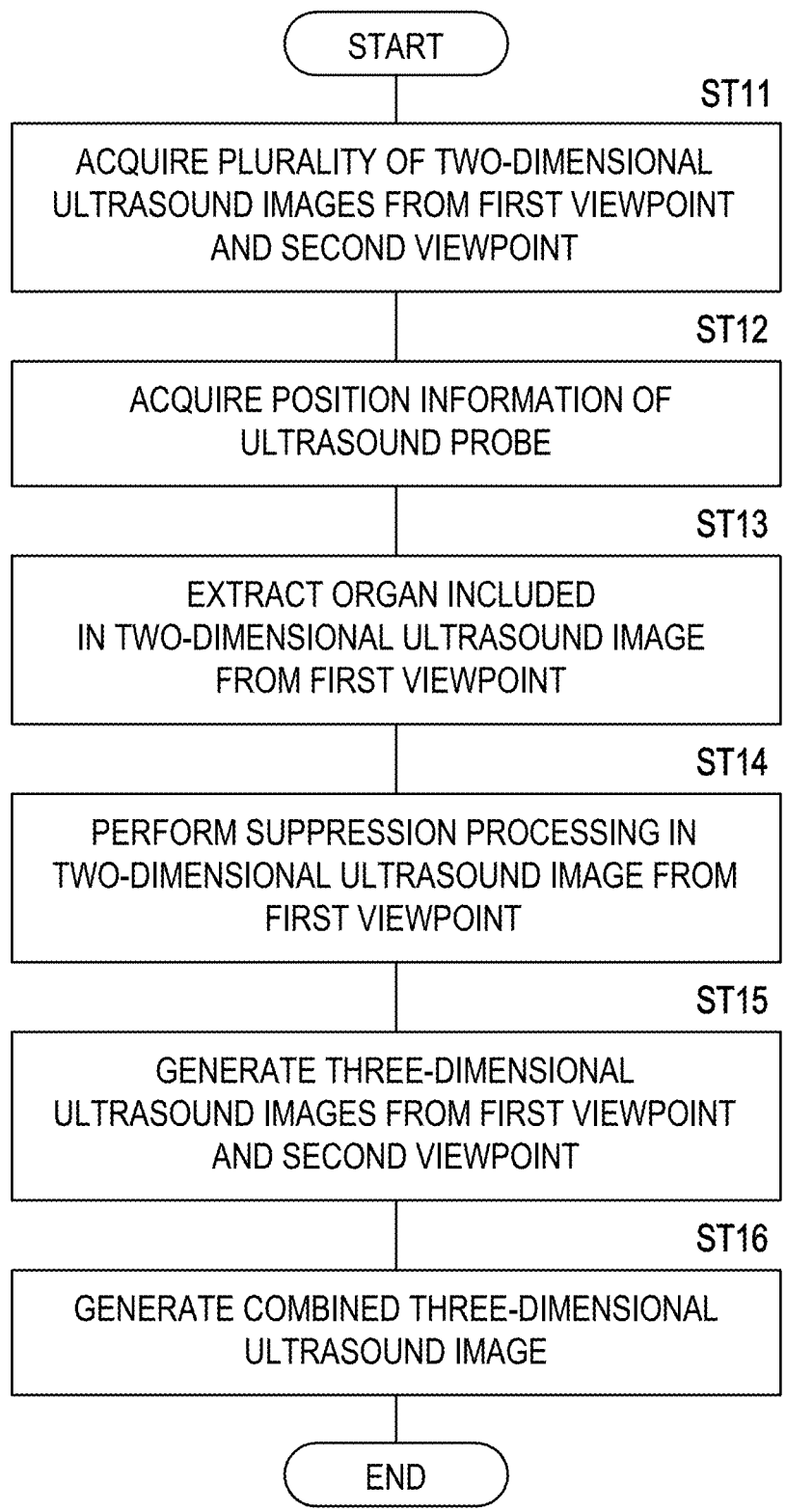
FIG. 16 is a flowchart illustrating processing performed in a second embodiment of the present disclosure.

Next, the three-dimensional ultrasound image generation apparatus according to a second embodiment will be described. The three-dimensional ultrasound image generation apparatus according to the second embodiment performs organ extraction and suppression processing on the two-dimensional ultrasound image P. The three-dimensional ultrasound image generation apparatus according to the second embodiment may have the same configuration as the three-dimensional ultrasound image generation apparatus 10 according to the first embodiment illustrated in FIG. 1. For this reason, a description of the configuration will be omitted, and only processing performed in the three-dimensional ultrasound image generation apparatus according to the second embodiment will be described. FIG. 16 is a flowchart illustrating processing performed in the second embodiment of the present disclosure.

In a case where the user operates the ultrasound probe 50 in a state where the ultrasound probe 50 is brought into contact with the body surface of the cervical portion M1 of the subject M, the image acquisition unit 21 acquires a plurality of two-dimensional ultrasound images P that are imaged from a viewpoint 1 and a viewpoint 2 which are different viewpoints (step ST11). The probe position information acquisition unit 22 acquires, for each imaging in step ST11, position information including an imaging direction indicating a direction of the viewpoint of the ultrasound probe 50 and an imaging position for each viewpoint (step ST12).

Next, the organ extraction unit 24 extracts a carotid artery M2 included in each of a plurality of two-dimensional ultrasound images P from the first viewpoint (step ST13). The image processing unit 25 extracts an unclear image region in each of the plurality of two-dimensional ultrasound images P from the first viewpoint, and performs suppression processing of deleting the extracted unclear image region (step ST14). Here, as illustrated in FIG. 10, the image processing unit 25 extracts, as an unclear image region, a region between the traveling direction of the ultrasound wave indicated by an arrow and the outer front surface of the carotid artery M2 (in FIG. 10, a region indicated by a shaded region) for all of the plurality of two-dimensional ultrasound images P from the first viewpoint.

The three-dimensional ultrasound image generation unit 23 generates three-dimensional ultrasound images VO1 and VO2 from the first viewpoint and the second viewpoint (step ST15). Here, since the three-dimensional ultrasound image VO1 from the first viewpoint is generated based on the plurality of two-dimensional ultrasound images P after the suppression processing from the first viewpoint, the three-dimensional ultrasound image VO1 from the first viewpoint does not include an unclear image region. That is, as in the three-dimensional ultrasound image VA1 after the suppression processing from the first viewpoint illustrated in the left part of FIG. 13, in the three-dimensional ultrasound image VO1 from the first viewpoint, an unclear image region is deleted.

Next, as illustrated in the right part of FIG. 12, the image combination unit 26 performs, on the three-dimensional ultrasound image VO2 from the second viewpoint, the same alignment processing as in the first embodiment, and generates a three-dimensional ultrasound image VA2 after the alignment processing from the second viewpoint on which the alignment processing is performed. The image combination unit 26 generates a combined three-dimensional ultrasound image VG (step ST16) by combining the deleted region in the three-dimensional ultrasound image VO1 from the first viewpoint from which the unclear image region is deleted with the region other than the unclear image region A2 in the three-dimensional ultrasound image VA2 after the alignment processing from the second viewpoint on which the alignment processing is performed. Thereafter, the process is ended.

As described above, in the second embodiment, an unclear image region in each of the plurality of two-dimensional ultrasound images P from the first viewpoint is extracted, and suppression processing of deleting the extracted unclear image region is performed. The three-dimensional ultrasound image VO1 from the first viewpoint is generated based on the plurality of two-dimensional ultrasound images P from the first viewpoint on which the suppression processing is performed, and is combined with the three-dimensional ultrasound image VO2 from the second viewpoint. As described above, even in a case where the suppression processing is performed on the two-dimensional ultrasound images P, a high-definition three-dimensional ultrasound image can be generated as in the first embodiment.

In the second embodiment, the plurality of two-dimensional ultrasound images P from the first viewpoint and the second viewpoint are acquired, and the three-dimensional ultrasound images V from the first viewpoint and the second viewpoint are generated. On the other hand, the technique of the present disclosure is not limited thereto. A plurality of two-dimensional ultrasound images P from three or more viewpoints may be acquired, and three-dimensional ultrasound images V from the first viewpoint and the second viewpoint may be generated. In this case, the suppression processing of suppressing unclearness in an unclear image region may be performed only in the plurality of two-dimensional ultrasound images P from the first viewpoint, the suppression processing may be performed in the plurality of two-dimensional ultrasound images P from two or more viewpoints, or the suppression processing may be performed in the plurality of two-dimensional ultrasound images P from all viewpoints.

Further, in the second embodiment, the organ extraction unit 24 can extract an organ in both of the two-dimensional ultrasound image P and the three-dimensional ultrasound image V. On the other hand, the technique of the present disclosure is not limited thereto. In a case where an organ is extracted only in the two-dimensional ultrasound image P as in the second embodiment, the organ extraction unit 24 may not have a function of extracting an organ in the three-dimensional ultrasound image V.

Further, in the first embodiment and the second embodiment, the image combination unit 26 may further perform averaging processing of averaging pixel values of pixels at the same positions with respect to pixel values of regions other than the region on which the suppression processing is performed, based on the three-dimensional ultrasound image VA1 after the suppression processing from the first viewpoint or the three-dimensional ultrasound image VO1 generated based on the plurality of two-dimensional ultrasound images P from the first viewpoint on which the suppression processing is performed, and the three-dimensional ultrasound image VA2 after the alignment processing from the second viewpoint. Thereby, a noise in the image can be reduced, and thus a higher-definition three-dimensional ultrasound image can be generated.

Further, in the first embodiment and the second embodiment, the image processing unit 25 deletes an unclear image region. On the other hand, the technique of the present disclosure is not limited thereto. The image processing unit 25 may decrease a pixel value of the unclear image region to be relatively lower than pixel values of other regions. As processing of decreasing a pixel value of the unclear image region, for example, processing of decreasing a pixel value of the unclear image region by setting a weight may be performed. Specifically, for example, processing of averaging a pixel value of the unclear image region and a pixel value of an image region other than the unclear image region at a ratio of 1:2 may be performed. Further, processing of decreasing a pixel value of the unclear image region by setting a weight according to a distance from a starting point of an artifact may be performed. Specifically, for example, processing of decreasing a pixel value of the unclear image region by setting a weight of the unclear image region to be larger as a distance from the ultrasound probe 50 increases may be performed. As a distance from the ultrasound probe 50 increases, the resolution of the image is lowered. Thus, by decreasing a pixel value of a region with lower resolution, the unclear image region may be further suppressed.

Further, in the first embodiment and the second embodiment, an embodiment in which one organ is extracted in the three-dimensional ultrasound image V has been described. On the other hand, the technique of the present disclosure is not limited to extraction of one organ. The technique described in the first embodiment may be applied to a case where two or more organs are extracted. In this case, processing of extracting and suppressing an unclear image region may be performed on each of the extracted organs.

Next, the three-dimensional ultrasound image generation apparatus according to a third embodiment will be described. The three-dimensional ultrasound image generation apparatus according to the third embodiment may have the same configuration as the three-dimensional ultrasound image generation apparatus 10 according to the first embodiment illustrated in FIG. 1. For this reason, a description of the configuration will be omitted, and only different portions will be described. The display control unit 27 of the three-dimensional ultrasound image generation apparatus according to the third embodiment controls the display unit 30 to display the three-dimensional ultrasound image V, and controls the display unit 30 to display the two-dimensional ultrasound images P from the first viewpoint and the second viewpoint which are imaged at imaging positions closest to a position designated by a user on the displayed three-dimensional ultrasound image V.

Figure 17:
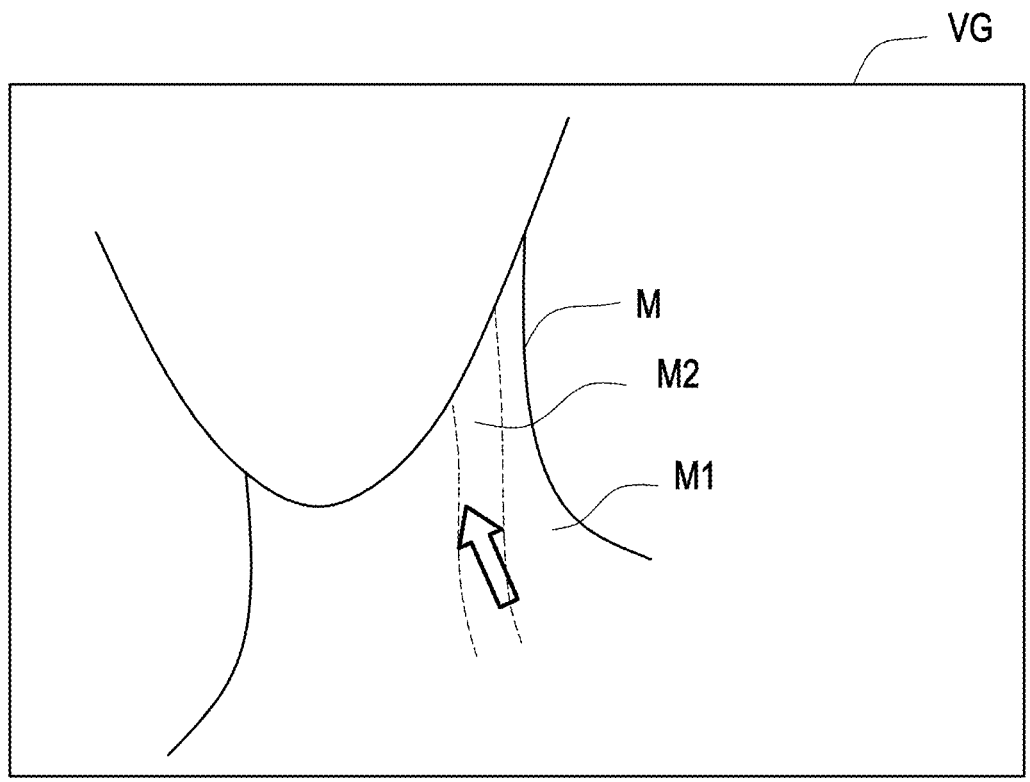
FIG. 17 is a diagram illustrating an example of a three-dimensional ultrasound image displayed on a display unit.
Figure 18:
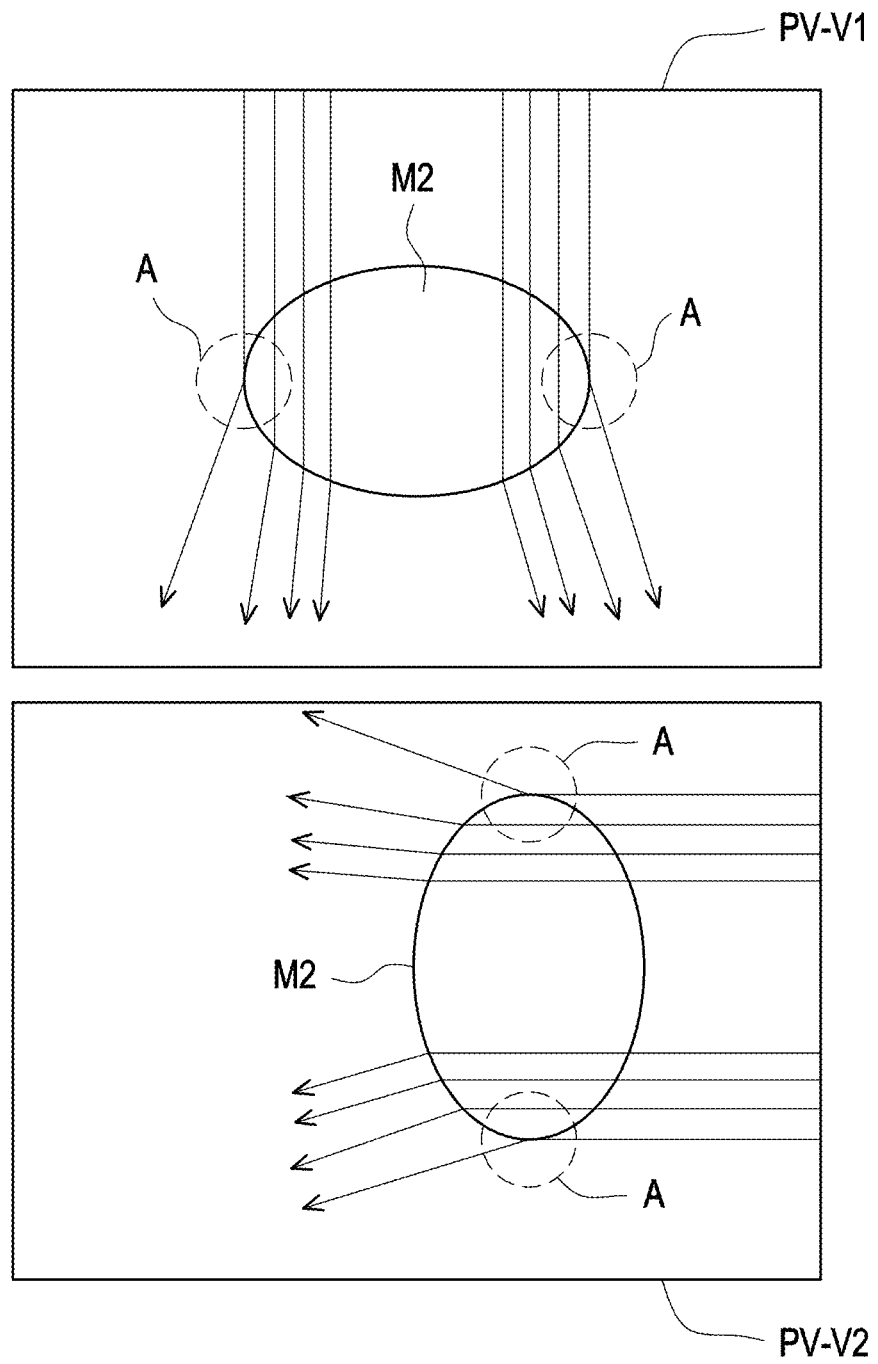
FIG. 18 is a diagram illustrating an example of a two-dimensional ultrasound image displayed on a display unit.

FIG. 17 is a diagram illustrating an example of the three-dimensional ultrasound image V displayed on the display unit, and FIG. 18 is a diagram illustrating an example of the two-dimensional ultrasound images P displayed on the display unit 30. As illustrated in FIG. 17, the user designates a certain position (as an example, an end portion of an arrow in FIG. 17) on the combined three-dimensional ultrasound image VG displayed on the display unit 30 by, for example, operating the input unit 40 such as a mouse.

The display control unit 27 extracts imaging positions closest to the designated position from the imaging positions stored in the primary storage unit 12, extracts the two-dimensional ultrasound images P from the first viewpoint and the second viewpoint that are stored in the primary storage unit 12 by being associated with the extracted imaging positions, and causes the display unit 30 to display the extracted two-dimensional ultrasound images P. The two-dimensional ultrasound images P from the first viewpoint and the second viewpoint may be displayed in parallel on the display unit 30, or may be alternately displayed so as to be switched according to a user's instruction.

As described above, the two-dimensional ultrasound image in which an unclear image region is not suppressed, that is, including an unclear image region such as an artifact, is displayed on the display unit 30. Thereby, it is possible to perform diagnosis capable of visually recognizing the original image, such as a degree of attenuation of an image signal.

Further, in the first embodiment and the second embodiment, the probe position information acquisition unit 22 derives information including the imaging position and the imaging direction of the ultrasound probe 50, from the position of the marker center 52a, and the positions, the sizes, and the inclinations of the markers 52x, 52y, and 52z in the captured image acquired by capturing the ultrasound probe 50 and the marker member 52 via the image capturing unit 60. On the other hand, the technique of the present disclosure is not limited thereto.

The probe position information acquisition unit 22 may acquire information including the imaging position and the imaging direction of the ultrasound probe 50 by using, for example, an augmented reality (AR) marker. The AR marker is an image including figures having a fixed pattern. The AR marker is provided on the outer circumferential surface of the ultrasound probe 50. By using a known program of detecting a position and a direction of the marker based on image data of the ultrasound probe 50 that includes the AR marker captured by the image capturing unit 60, the AR marker, that is, the information including the imaging position and the imaging direction of the ultrasound probe 50, may be acquired.

Further, instead of the marker member 52, a projection portion and a recess portion may be provided on a main body of the ultrasound probe 50. In this case, information including the imaging position and the imaging direction of the ultrasound probe 50 may be derived by using, as markers, the projection portion and the recess portion. In the technique of the present disclosure, the marker may have any shape and any form as long as the marker can be used as an index for defining the imaging position and the imaging direction of the ultrasound probe 50, and is not particularly limited.

Further, for example, the diagnosis support system 1 may include a sensor instead of the image capturing unit 60 and the marker member 52.

Figure 19:
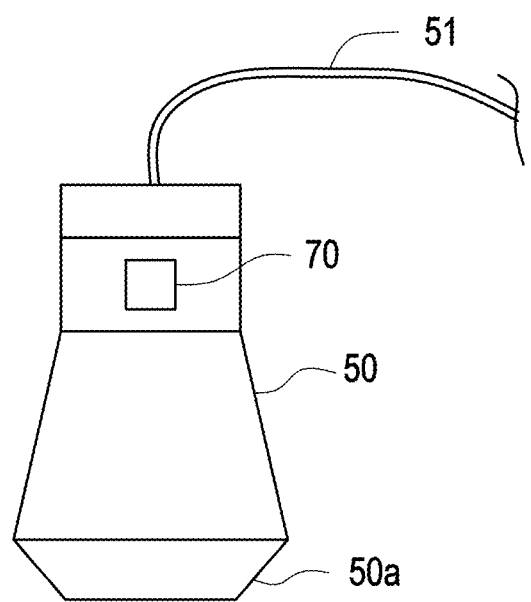
FIG. 19 is a diagram for explaining the ultrasound probe including a sensor.

FIG. 19 is a diagram for explaining the ultrasound probe including a sensor. In FIG. 19, attachment of a sensor to the ultrasound probe 50 is simply illustrated, unlike the actual shape.

As illustrated in FIG. 19, the ultrasound probe 50 includes a sensor 70 attached to the outer circumferential surface of the ultrasound probe 50. The sensor 70 is a six-axis sensor that can detect a moving direction, a direction, and a rotation and can further calculate a moving distance, a moving speed, and the like. The six-axis sensor is realized by combining an acceleration sensor that can detect three directions of a direction of front and back, a direction of right and left, and a direction of up and down with a geomagnetic sensor that can detect directions of north, south, east, and west, or combining an acceleration sensor with a gyro sensor that can detect a speed of rotation.

The probe position information acquisition unit 22 can acquire the imaging position based on output information which is output from the sensor 70.

In the embodiment, the sensor 70 is provided instead of the image capturing unit 60 and the marker member 52. On the other hand, the technique of the present disclosure is not limited thereto. The sensor 70 may be provided in addition to the image capturing unit 60 and the marker member 52. In this case, the sensor 70 is suitable for detecting the imaging direction of the ultrasound probe 50, and a method of calculating the imaging position from the captured image acquired by capturing the ultrasound probe 50 and the marker member 52 via the image capturing unit 60 is suitable for detecting a parallel movement of the ultrasound probe 50. Thus, by using the image capturing unit 60, the marker member 52, and the sensor 70, the probe position information acquisition unit 22 can acquire the imaging position and the imaging direction with higher accuracy.

Further, in the above-described embodiment, for example, the following various processors may be used as a hardware structure of processing units performing various processing, such as the image acquisition unit 21, the probe position information acquisition unit 22, the three-dimensional ultrasound image generation unit 23, the organ extraction unit 24, the image processing unit 25, the image combination unit 26, and the display control unit 27. The various processors include, as described above, a CPU, which is a general-purpose processor that functions as various processing units by executing software (programs), and a dedicated electric circuit, which is a processor having a circuit configuration specifically designed to execute a specific processing, such as a programmable logic device (PLD) or an application specific integrated circuit (ASIC) that is a processor of which the circuit configuration may be changed after manufacturing such as a field programmable gate array (FPGA).

One processing unit may be configured by one of these various processors, or may be configured by a combination of two or more processors having the same type or different types (for example, a combination of a plurality of FPGAs or a combination of a CPU and an FPGA). Further, the plurality of processing units may be configured by one processor.

As an example in which the plurality of processing units are configured by one processor, firstly, as represented by a computer such as a client and a server, a form may be adopted in which one processor is configured by a combination of one or more CPUs and software and the processor functions as the plurality of processing units. Secondly, as represented by a system on chip (SoC) or the like, a form may be adopted in which a processor that realizes the function of the entire system including the plurality of processing units by one integrated circuit (IC) chip is used. As described above, the various processing units are configured by using one or more various processors as a hardware structure.

Further, as the hardware structure of the various processors, more specifically, an electric circuit (circuitry) in which circuit elements such as semiconductor elements are combined may be used.

EXPLANATION OF REFERENCES

1: diagnosis support system
10: three-dimensional ultrasound image generation apparatus
11: CPU
12: primary storage unit
13: secondary storage unit
14: external I/F
15: three-dimensional ultrasound image generation program
16: bus line
17: transmission/reception unit
21: image acquisition unit
22: probe position information acquisition unit
23: three-dimensional ultrasound image generation unit
24: organ extraction unit
25: image processing unit
26: image combination unit
27: display control unit
30: display unit
40: input unit
50: ultrasound probe
50a: transducer array
51: cable
52: marker member
60: image capturing unit
70: sensor
M: subject
M1: cervical portion
M2: carotid artery
H: hand
P: two-dimensional ultrasound image
V: three-dimensional ultrasound image
VA1, VA2: three-dimensional ultrasound image after suppression processing
VO1, VO2: three-dimensional ultrasound image
VG: combined three-dimensional ultrasound image
α: angle

What is claimed is:

1. A three-dimensional ultrasound image generation apparatus comprising a processor,
the processor configured to:
acquire a plurality of two-dimensional ultrasound images from each of a first viewpoint and a second viewpoint by imaging an organ in a subject at a plurality of imaging positions while moving an ultrasound probe in one direction along a body surface of the subject, the plurality of two-dimensional ultrasound images being acquired by performing imaging at the plurality of imaging positions from each of at least two viewpoints of the first viewpoint and the second viewpoint;
acquire, for each imaging, position information including an imaging direction indicating a direction of the viewpoint of the ultrasound probe and the imaging position for each viewpoint;
extract the organ included in the two-dimensional ultrasound images based on at least one two-dimensional ultrasound image among the plurality of two-dimensional ultrasound images from at least one viewpoint of the first viewpoint or the second viewpoint;
extract an unclear image region from each of the plurality of two-dimensional ultrasound images corresponding to the viewpoint of the two-dimensional ultrasound image from which at least the organ is extracted among the two-dimensional ultrasound images from each of the first viewpoint and the second viewpoint, based on position information of the organ and the position information of the ultrasound probe, and perform suppressing the unclear image region in the extracted image region, wherein the unclear image region comprises an artifact caused by reflection or refraction of an ultrasound wave;
generate three-dimensional ultrasound images from two viewpoints of the first viewpoint and the second viewpoint based on each of the plurality of two-dimensional ultrasound images from two viewpoints of the first viewpoint and the second viewpoint, the two-dimensional ultrasound image on which the suppression processing is performed being included in the two-dimensional ultrasound images from at least one viewpoint among the two-dimensional ultrasound images from two viewpoints; and
generate a combined three-dimensional ultrasound image by combining the three-dimensional ultrasound images from two viewpoints of the first viewpoint and the second viewpoint,
wherein the processor further is configured to perform averaging processing of averaging pixel values of pixels at the same positions based on the three-dimensional ultrasound image from two viewpoints of the first viewpoint and the second viewpoint, the averaging processing being processing of averaging the pixel values of regions other than the unclear image region on which the suppression processing is performed,
wherein the three-dimensional ultrasound image generation apparatus further comprises:
a marker member that is fixed to the ultrasound probe;
a camera that captures an image of the ultrasound probe and the marker member within a same image capturing range as the image of the ultrasound probe; and
a sensor, which is different from the camera, is configured to detect the imaging direction of the ultrasound probe,
wherein the processor is configured to acquire the position information of the ultrasound probe based on the captured image of the ultrasound probe and the marker member which is acquired by the camera.

2. The three-dimensional ultrasound image generation apparatus according to claim 1,
wherein the processor is configured to extract the unclear image region based on a traveling direction of the ultrasound wave emitted from the ultrasound probe to the organ, the traveling direction of the ultrasound wave being derived based on the position information of the organ extracted and the position information of the ultrasound probe.

3. The three-dimensional ultrasound image generation apparatus according to claim 2,
wherein the processor is configured to extract, as the unclear image region, a region in which an angle formed by the traveling direction of the ultrasound wave and an outer front surface of the organ is equal to or smaller than a predetermined threshold value.

4. The three-dimensional ultrasound image generation apparatus according to claim 1,
wherein the suppression processing is processing of decreasing a pixel value of the unclear image region to be relatively lower than pixel values of other regions.

5. The three-dimensional ultrasound image generation apparatus according to claim 1, the processor is further configured to:
cause a display to display at least one image of the two-dimensional ultrasound image or the three-dimensional ultrasound image,
wherein the processor is configured to control the display to display the combined three-dimensional ultrasound image, and controls the display to display the two-dimensional ultrasound images which are imaged at imaging positions closest to a position designated by a user on the combined three-dimensional ultrasound image which is displayed.

6. A three-dimensional ultrasound image generation method comprising:
acquiring a plurality of two-dimensional ultrasound images from each of a first viewpoint and a second viewpoint by imaging an organ in a subject at a plurality of imaging positions while moving an ultrasound probe in one direction along a body surface of the subject, the plurality of two-dimensional ultrasound images being acquired by performing imaging at the plurality of imaging positions from each of at least two viewpoints of the first viewpoint and the second viewpoint;
acquiring, for each imaging, position information including an imaging direction indicating a direction of the viewpoint of the ultrasound probe and the imaging position for each viewpoint;
extracting the organ included in the two-dimensional ultrasound images based on at least one two-dimensional ultrasound image among the plurality of acquired two-dimensional ultrasound images from at least one viewpoint of the first viewpoint or the second viewpoint;
extracting an unclear image region from each of the plurality of two-dimensional ultrasound images corresponding to the viewpoint of the two-dimensional ultrasound image from which at least the organ is extracted among the two-dimensional ultrasound images from each of the first viewpoint and the second viewpoint, based on position information of the organ having been extracted and the acquired position information of the ultrasound probe, and suppressing the unclear image region in the extracted image region, wherein the unclear image region comprises an artifact caused by reflection or refraction of an ultrasound wave;
generating three-dimensional ultrasound images from two viewpoints of the first viewpoint and the second viewpoint based on each of the plurality of two-dimensional ultrasound images from two viewpoints of the first viewpoint and the second viewpoint, the two-dimensional ultrasound image on which the suppression processing is performed being included in the two-dimensional ultrasound images from at least one viewpoint among the two-dimensional ultrasound images from two viewpoints;
generating a combined three-dimensional ultrasound image by combining the generated three-dimensional ultrasound images from two viewpoints of the first viewpoint and the second viewpoint,
performing averaging processing of averaging pixel values of pixels at the same positions based on the three-dimensional ultrasound image from two viewpoints of the first viewpoint and the second viewpoint, the averaging processing being processing of averaging the pixel values of regions other than the unclear image region on which the suppression processing is performed,
capturing an image of the ultrasound probe and a marker member within a same image capturing range as the image of the ultrasound probe, wherein the marker member is fixed to the ultrasound probe;
detecting the imaging direction of the ultrasound probe by using a sensor which is different from the camera; and
acquiring the position information of the ultrasound probe based on the captured image of the ultrasound probe and the marker member which is acquired by the camera.

7. A non-transitory computer readable recording medium storing a three-dimensional ultrasound image generation program performing the three-dimensional ultrasound image generation method according to claim 6.

* * * * *